(12) United States Patent
Suzuki et al.

(10) Patent No.: US 6,215,137 B1
(45) Date of Patent: Apr. 10, 2001

(54) MICROMECHANICAL SENSOR FOR SCANNING THERMAL IMAGING MICROSCOPE AND METHOD OF MAKING THE SAME

(75) Inventors: Yoshihiko Suzuki; Shinya Hara, both of Chiba (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/132,762

(22) Filed: Aug. 12, 1998

(30) Foreign Application Priority Data

Sep. 12, 1997 (JP) .................................................. 9-267725

(51) Int. Cl.[7] .................................................. H01L 27/20
(52) U.S. Cl. .......................... 257/254; 257/253; 257/254; 257/417; 257/418; 257/419; 257/420
(58) Field of Search ..................... 257/253, 254, 257/417, 418, 419, 420

(56) References Cited

U.S. PATENT DOCUMENTS

| 5,116,462 | 5/1992 | Bartha et al. ........................ 156/643 |
|---|---|---|
| 5,614,742 | * 3/1997 | Gessner et al. ....................... 257/254 |
| 5,619,050 | * 4/1997 | Uenoyama et al. .................. 257/254 |
| 5,629,538 | * 5/1997 | Lipphardt et al. .................... 257/254 |
| 5,635,739 | * 6/1997 | Grieff et al. .......................... 257/254 |

FOREIGN PATENT DOCUMENTS

002249665 * 5/1992 (GB) .................................... 257/254

OTHER PUBLICATIONS

Yoshihiko Suzuki, "Jpn. J. Appl. Phys.", 35, Novel Microcantilever for Scanning Thermal Imaging Microscopy, Mar. 1, 1996, pp. L352–L354, Part 2, No. 3A.

* cited by examiner

Primary Examiner—Eddie C. Lee
Assistant Examiner—Edgardo Ortiz
(74) Attorney, Agent, or Firm—Foley & Lardner

(57) ABSTRACT

A probe is provided with a thermocouple made of a joint between a first metal material and a second metal material. The first metal material is formed on the surface of a flexible plate facing a substrate, continuously from the thermocouple portion. The surface of the flexible plate facing the substrate is formed with a first wiring conductive film, which is electrically connected to the first metal material and extends over the proximal end side area of the flexible plate.

6 Claims, 20 Drawing Sheets

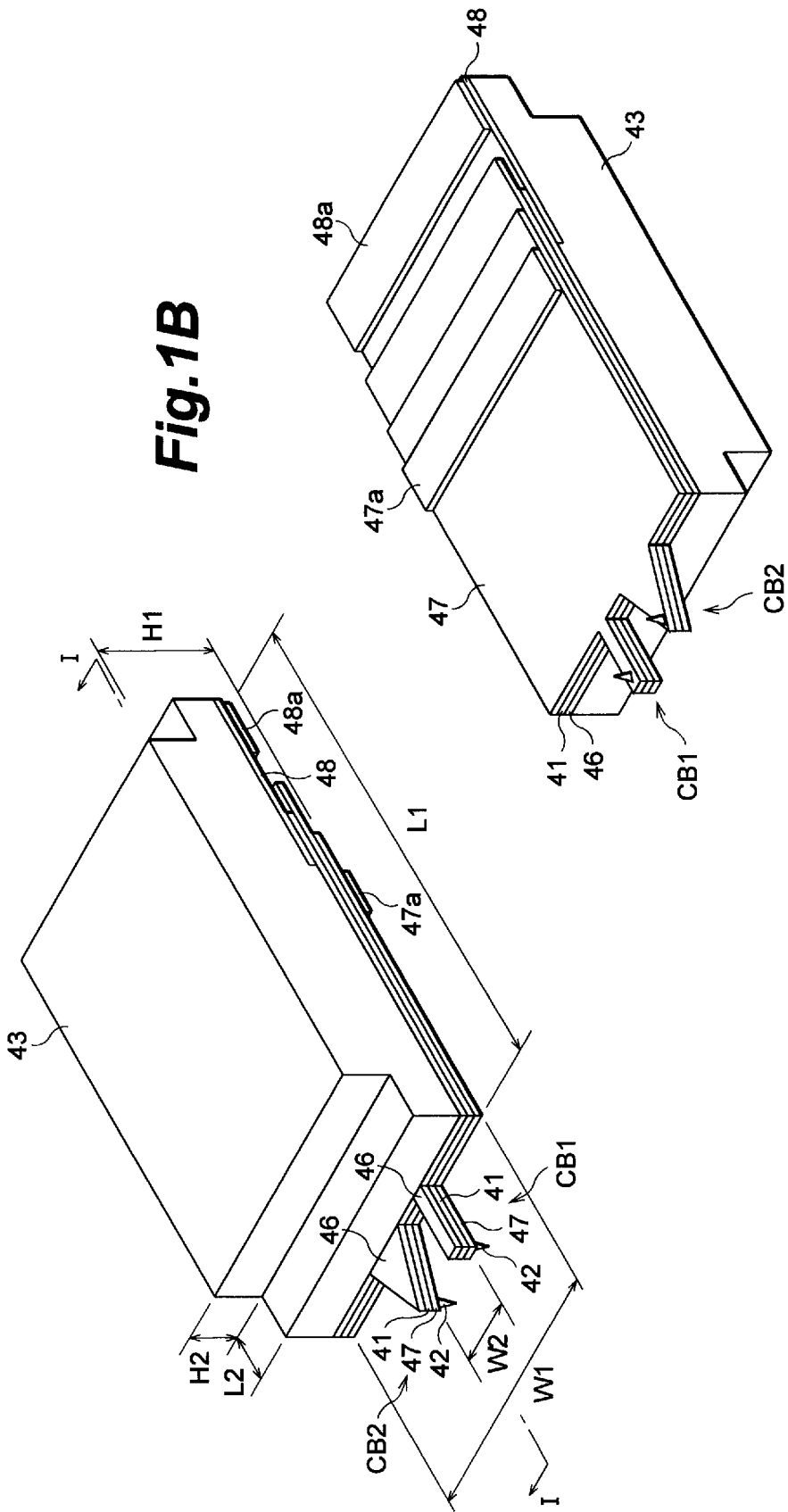

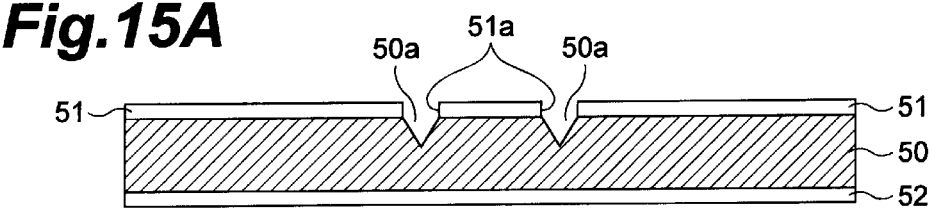
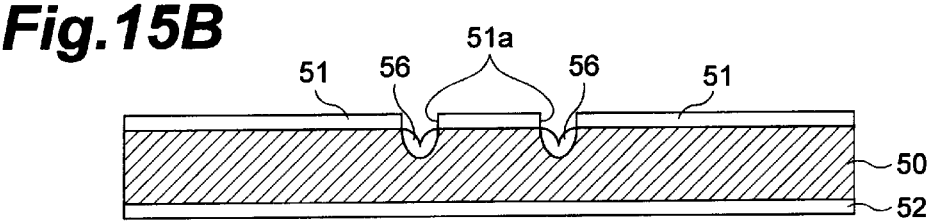
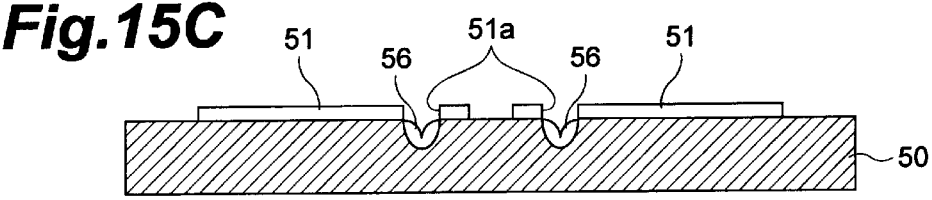
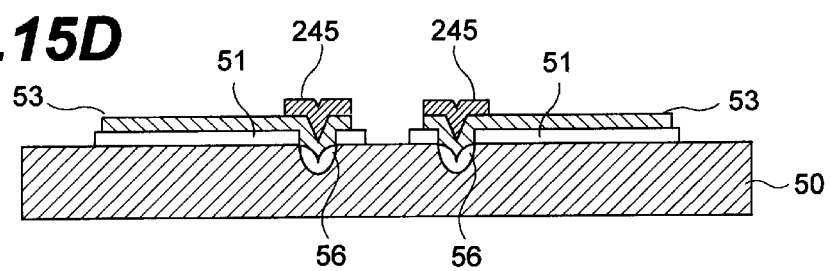
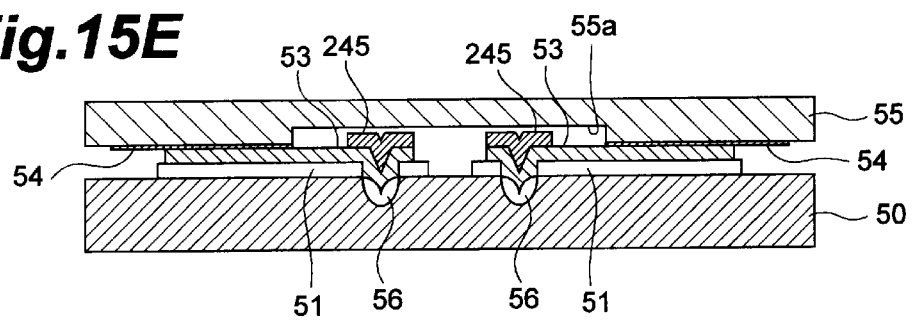
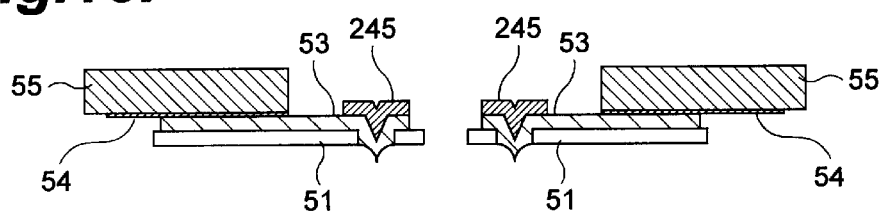

MICROMECHANICAL SENSOR FOR SCANNING THERMAL IMAGING MICROSCOPE AND METHOD OF MAKING THE SAME

BACKGROUND OF THE INVENTION

1. Field of the Invention

The present invention relates to a micromechanical sensor used for a scanning probe microscope and a method of making the same; and, in particular, to a micromechanical sensor suitable for a scanning thermal imaging microscope and a method of making the same.

2. Related Background Art

In recent years, scanning probe microscopes using physicochemical actions between a probe and a sample have been studied actively. In particular, scanning thermal imaging (STI) microscopes for measuring temperature distribution or thermal conductivity distribution in sample surfaces are considered to be promising as a technology for analyzing semiconductor operations or a technology for analyzing thermal characteristics of materials. An STI microscope developed by the inventor is disclosed in *Jpn. J. Appl. Phys.*, Vol. 35 (1996), pp.L352–L354.

SUMMARY OF THE INVENTION

The micromechanical sensor of the present invention has a plurality of cantilever beams extending from a substrate. Each cantilever beam has a different resonance frequency. A cantilever needed for the aimed measurement is selected, and the unselected cantilevers are broken off and removed from the substrate upon use. The lower face of the substrate is provided with a bonding pad. The bonding pad is made of Au/NiCr or the like. The bonding pad is formed by the steps of initially placing a semiconductor mask over the lower face of the substrate with a space therebetween, and then depositing a bonding pad material onto the lower face of the cantilever beam by way of the semiconductor mask. The outer periphery of a wafer to be provided with the cantilever beam is formed with a positioning recess, and the outer periphery of the semiconductor mask is also formed with a positioning recess. A ball bearing or supporting pin is disposed between these positioning recesses so as to position the wafer and the semiconductor mask with respect to each other.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1A is a perspective view of a micromechanical sensor in accordance with an embodiment;

FIG. 1B is a perspective view of the micromechanical sensor shown in FIG. 1A as observed from the rear side;

FIGS. 15A, 15B, 15C, 15D, 15E, and 15F are schematic sectional views showing another example of process for making the micromechanical sensor shown in FIG. 13A;

DETAILED DESCRIPTION OF THE PREFERRED EMBODIMENTS

Figure 1C:
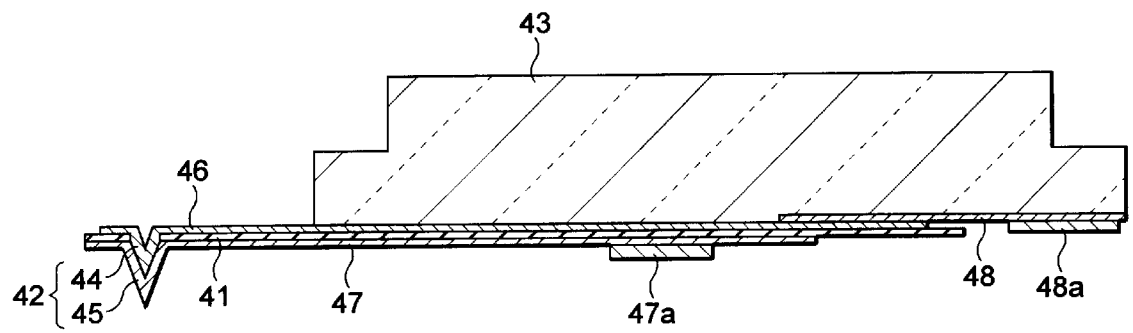
FIG. 1C is a sectional view of the micromechanical sensor shown in FIG. 1A taken along the arrowed line I—I.

In the following, preferred embodiments of the present invention will be explained with reference to the accompanying drawings. Constituents identical to each other will be referred to with numerals or letters identical to each other without repeating their overlapping explanations. FIG. 1A is a perspective view of the micromechanical sensor in accordance with an embodiment. FIG. 1B is a perspective view of the micromechanical sensor shown-in FIG. 1A as observed from the rear side. In the following explanation, "sectional view" indicates "end view." FIG. 1C is a sectional view of the micromechanical sensor shown in FIG. 1A taken along the arrowed line I—I. This micromechanical sensor, whose width W1=1.6 mm, width W2=0.6 mm, length L1=3.6 mm, length L2=250 $\mu$m, length L3=900 $\mu$m, thickness H1=500 $\mu$m, and thickness H2=250 $\mu$m, has a very small size and is manufactured by a semiconductor process capable of minute processing.

The micromechanical sensor in accordance with this embodiment has a plurality of cantilever beams CB1, CB2 extending from a substrate 43. The cantilever beams CB1, CB2 have resonance frequencies different from each other. A probe needed for the aimed measurement is selected, and the unselected probe is broken off and removed from the substrate upon use.

Each cantilever beam CB1, CB2 comprises a flexible plate (insulating film) 41 (SiNx: silicon nitride) having an opening at a tip thereof, wiring conductive films 46 and 47 (NiCr and Ti) respectively formed on the upper and lower faces of the flexible plate 41, and a thermocouple 42 projecting downward from within the opening of the flexible plate 41. The thermocouple 42 is constituted by different kinds of metal materials 44, 45 (NiCr/Ti). In this embodiment, the wiring conductive film 46 and the metal material 44 are made of an identical material, whereas the wiring conductive film 47 and the metal material 45 are made of an identical material. The wiring conductive films 46, 47 of one cantilever beam CB1 are electrically connected to those of the other cantilever beam CB2, such that their wiring conductive film 46 located directly below the substrate 43, as well as their wiring conductive film 47 located directly below the substrate 43, is used in common. Since the cantilever beams CB1, CB2 have the same configuration except that their resonance frequencies differ from each other, only the configuration of one cantilever beam will be explained in the following without explaining the other cantilever beam.

The micromechanical sensor in accordance with this embodiment comprises the flexible plate 41 made of an insulating material; the tip portion (probe) 42 made of a thermocouple projecting from the lower face of a tip side area of the flexible plate 41; and the substrate 43, made of an insulating material, joined to the upper face of a proximal end side area of the flexible plate 41. Accordingly, the probe 42 and the substrate 43 project from the flexible plate 41 in the directions opposite to each In this embodiment, the probe 42 is constituted by different kinds of metal films (metal materials) 44, 45, whereby the joint between the metal films 44, 45 in the probe 42 forms a thermocouple. It is not necessary for the whole probe 42 to be constituted by the metal films 44, 45, though. For example, only a part of the probe 42 may be made of a different kind of metal film as well. In the flexible plate 41, the metal film 44 projects downward from an opening formed at a part corresponding to the probe 42.

The metal film 44 is formed on the upper face (surface facing the substrate 43) of the flexible plate 41, continuously from the thermocouple portion. The upper face of the flexible plate 41 is formed with the wiring conductive film (NiCr) 46, which is electrically connected to the metal film 44 and extends over the proximal end side area of the flexible plate 41. In this embodiment, the wiring conductive film 46 is formed as a direct extension of the metal film 44. The wiring conductive film 46, however, may also be made of a metal material different from that of the metal film 44, a plurality films patched together, or a multilayer film.

The metal film 45 is formed on the lower face (surface facing the probe 42) of the flexible plate 41, continuously from the thermocouple portion. The lower face of the flexible plate 41 is formed with the wiring conductive film (Ti) 47, which is electrically connected to the metal film 45 and extends over the proximal end side area of the flexible plate 41. In this embodiment, the wiring conductive film 47 is formed as a direct extension of the metal film 45. The wiring conductive film 47, however, may also be made of a metal material different from that of the metal film 45, a plurality films patched together, or a multilayer film.

The lower face (surface facing the flexible plate 41) of the substrate 43 is formed with a wiring conductive film (Au/NiCr) 48, made of a metal film, extending from an area overlapping with the flexible plate 41 to an area not overlapping with the flexible plate 41. An end portion of the wiring conductive film 48 in the non-overlapping area constitutes an electrode pad portion (bonding pad) 48a for electric connection with the outside. For example, the electrode pad portion 48a is made of a material such as gold or aluminum deposited on the wiring conductive film 48. Of course, the electrode pad portion 48a may be made of the same material as the wiring conductive film 48, e.g., Au/NiCr, or a part of the wiring conductive film 48 may constitute the electrode pad 48a. In this embodiment, the wiring conductive film 48 constitutes a conductor for external connection, a part of which is disposed so as to electrically connect with the wiring conductive film 46, while another part is lead to the outside. A conductor such as metal foil, wire, or the like may also be used as the conductor for external connection, though.

A part of the flexible plate 41 and wiring conductive film 46 is joined to the substrate 43 such that the wiring conductive film 46 and the wiring conductive film 48 are electrically connected to each other. In this embodiment, the substrate 43 is made of a glass material (e.g., borosilicate glass) containing a movable ion, and the flexible plate 41 and the substrate 43 are joined together by anode coupling. Nevertheless, the substrate 43 may also be made of other insulating materials, and the joint between the flexible plate 41 and the substrate 43 is not always restricted to anode coupling. Specifically, as an example of the above-mentioned glass material, Pyrex glass (product name) may be mentioned.

Though the substrate 43 made of an insulating material is thus used in this embodiment, the one made of a conductive material such as a metal or the like may also be used. In this case, the wiring conductive film 48 is eliminated, and the flexible plate 41 and the wiring conductive film 46 are joined together such that the substrate 43 and the wiring conductive film 46 are electrically connected to each other. Formed on the wiring conductive film 47 is an electrode pad 47a made of Au/NiCr. The electrode pad 47a may be made of aluminum. As the voltage between the electrode pads 47a and 48a is measured, electromotive force of the thermocouple 42, i.e., temperature of the thermocouple 42, can be determined. In this embodiment, as the metals 44 and 45 constituting the projecting thermocouple 42, NiCr and Ti are used, respectively.

The following combinations of the metals 44 and 45 may also be used. Namely, as different kinds of metal materials which can constitute the thermocouple 42, (1) Pt and Pt/Rh, (2) Chromel and Alumel, (3) Cu and Constantan, or the like can be used as well.

As different kinds of metal materials which can constitute the thermocouple 42, two different kinds of materials selected from the group consisting of Mg, Al, Si, Ti, V, Cr, Mn, Fe, Co, Ni, Cu, Zn, Ga, Ge, Mo, Pd, Ag, Cd, In, Sn, Sb, Te, W, Ta, Ir, Pt, Au, Pd, and Rh may be used.

As different kinds of metal materials which can constitute the thermocouple 42, an alloy (A) containing at least two different kinds of materials selected from the group consisting of Mg, Al, Si, Ti, V, Cr, Mn, Fe, Co, Ni, Cu, Zn, Ga, Ge, Mo, Pd. Ag, Cd, In, Sn, Sb, Te, W, Ta, Ir, Pt, Au, Pd, and Rh; and an alloy (B), different from the alloy (A), containing at least two kinds of materials selected from this group may be used.

As different kinds of metal materials which can constitute the thermocouple 42, an alloy (A) containing at least two different kinds of materials selected from the group consisting of Mg, Al, Si, Ti, V, Cr, Mn, Fe, Co, Ni, Cu, Zn, Ga, Ge, Mo, Pd, Ag, Cd, In, Sn, Sb, Te, W, Ta, Ir, Pt, Au, Pd, and Rh; and a single metal, different from the alloy (A), selected from this group may be used.

The flexible plate 41 is an insulating film, which is made of SiNx in this embodiment, may also be made of $SiO_2$.

The micromechanical sensor in accordance with this embodiment is configured as a micromechanical sensor for a microscope which can achieve functions of both scanning heat measurement microscope and scanning atomic force microscope. The scanning atomic force microscope is disclosed in U.S. Pat. No. 5,116,462, which is incorporated herein by reference for the explanation thereof.

A method of making the above-mentioned micromechanical sensor will now be explained with reference to FIGS. 2A to 9B.

Figure 2A:
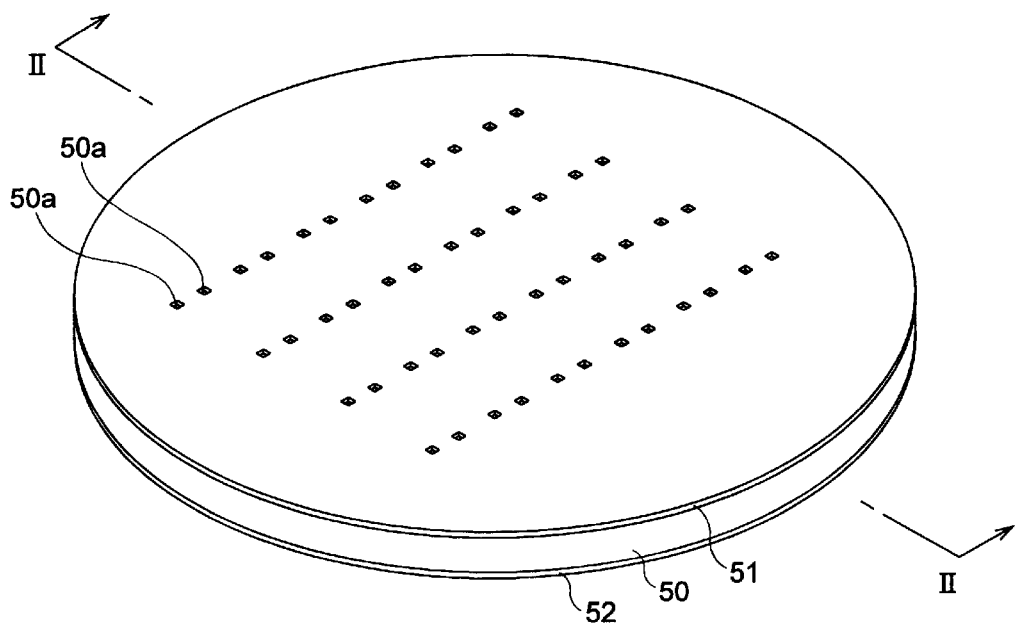
FIG. 2A is a perspective view of a micromechanical sensor intermediate group for explaining a method of making the micromechanical sensor.
Figure 2B:
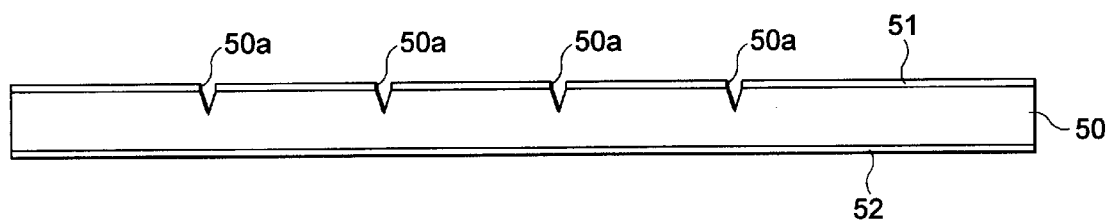
FIG. 2B is a sectional view of the intermediate group shown in FIG. 2A taken along the arrowed line II—II.

FIG. 2A is a perspective view of a micromechanical sensor intermediate group for explaining this method, whereas FIG. 2B is a sectional view of the intermediate group shown in FIG. 2A taken along the arrowed line II—II. In order to make the micromechanical sensor in accordance with the above-mentioned embodiment, a semiconductor wafer (substrate) 50 made of Si is initially prepared. Then, SiNx films 51, 52 are respectively formed on both sides of the wafer 50 by low pressure CVD (LPCVD) technique. Further, lithography technique is used for forming a plurality of rectangular openings 50a in the SiNx films 51, 52, so that the surface areas of the wafer 50 within the rectangular openings 50a are exposed. Thereafter, an etchant (etching liquid) is brought into contact with the surface areas of the wafer 50 in the rectangular openings 50a so that these areas are anisotropically etched, thereby forming depressions (cavities) each shaped like an inverted pyramid.

Figure 3A:
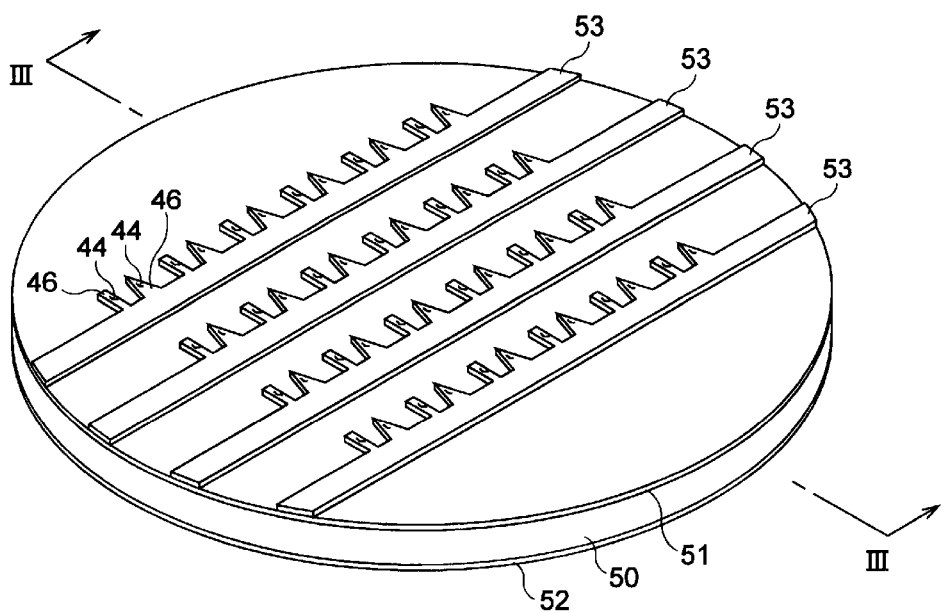
FIG. 3A is a perspective view of a micromechanical sensor intermediate group.
Figure 3B:
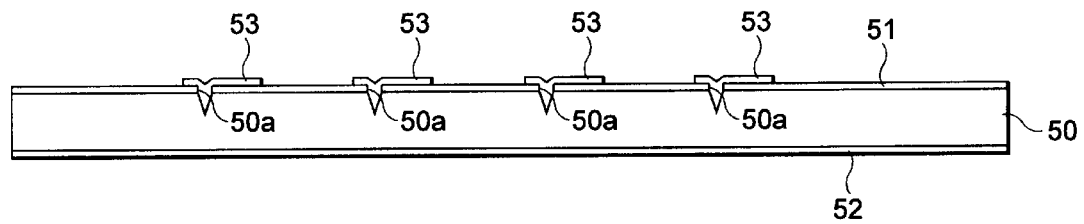
FIG. 3B is a sectional view of the intermediate group shown in FIG. 3A taken along the arrowed line III—III.

FIG. 3A is a perspective view of a micromechanical sensor intermediate group, whereas FIG. 3B is a sectional view of the intermediate group shown in FIG. 3A taken along the arrowed line III—III. Next, lift-off technique is used for forming an NiCr film 53 on the wafer 50. The NiCr film 53 includes a thermocouple metal material portion 44 covering the minute surface area within the cavity in each of the plurality of rectangular openings 50a, and a wiring conductive material portion 46 covering an area extending outward from within each cavity.

Figure 4A:
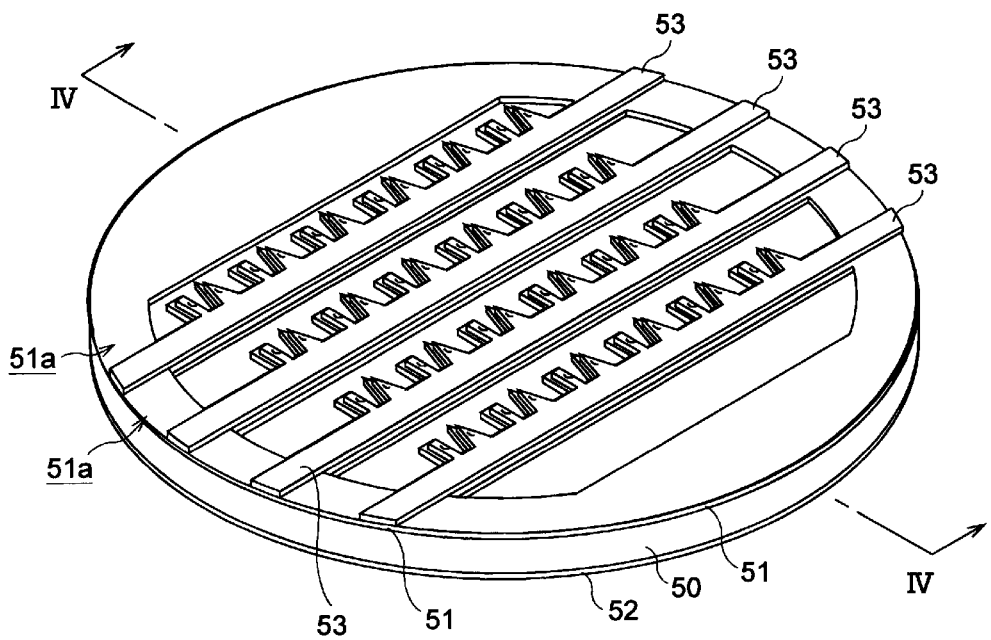
FIG. 4A is a perspective view of a micromechanical sensor intermediate group.
Figure 4B:
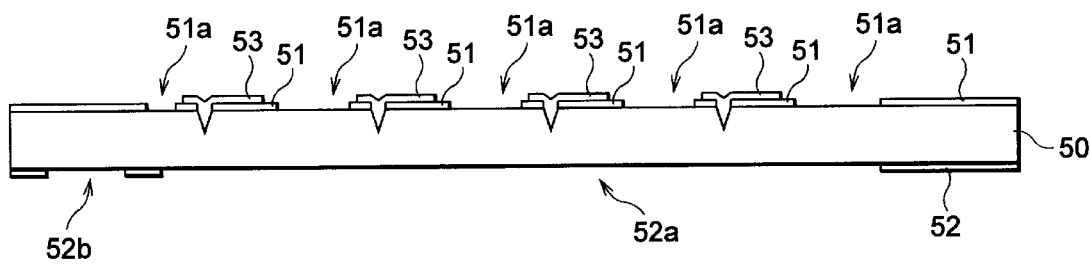
FIG. 4B is a sectional view of the intermediate group shown in FIG. 4A taken along the arrowed line IV—IV.

FIG. 4A is a perspective view of a micromechanical sensor intermediate group, whereas FIG. 4B is a sectional view of the intermediate group shown in FIG. 4A taken along the arrowed line IV—IV. Next, photolithography technique is used for etching a plurality of areas extending in the widthwise direction of the upper SiNx film 51, so as to form stripe-like opening areas 51a physically separating the NiCr films 53, for a micromechanical sensor intermediate array, extending in parallel to each other in the widthwise direction, from each other along the lengthwise direction, thereby exposing the wafer upper face from within the stripe-like opening areas 51a. The stripe-like opening areas 51a at both ends in the lengthwise direction each separate the outermost SiNx film 51 and its adjacent NiCr film 53 from each other. The SiNx film 52 on the rear side is etched such that the SiNx film 52 is left-like a ring along the outer periphery of the wafer 50, thus forming a center opening 52a and exposing the rear face of the wafer 50 from within the center opening 52a. Also, positioning openings 52b are respectively formed within a plurality of areas of the ring-like SiNx film 52, whereby the rear face of the wafer 50 are exposed from within the positioning openings 52b.

Figure 5A:
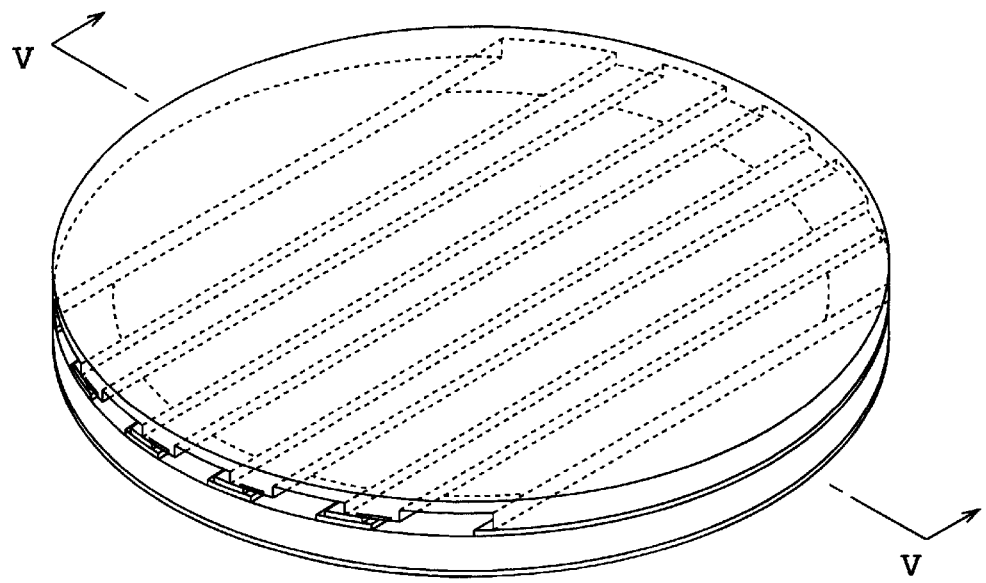
FIG. 5A is a perspective view of a micromechanical sensor intermediate group.
Figure 5B:
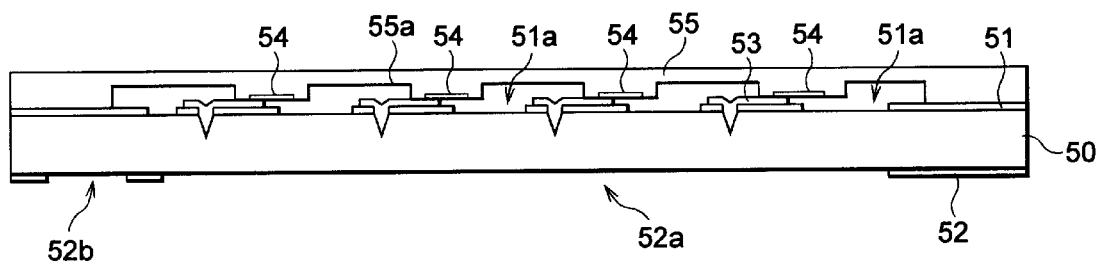
FIG. 5B is a sectional view of the intermediate group shown in FIG. 5A taken along the arrowed line V—V.

FIG. 5A is a perspective view of a micromechanical sensor intermediate group, whereas FIG. 5B is a sectional view of the intermediate group shown in FIG. 5A taken along the arrowed line V—V. Next, a glass member 55 having a plurality of grooves 55a formed along the widthwise direction is prepared. The deepest part of the groove 55a is located at a position depressed from the flat face 55b of the glass member 55 by a predetermined distance. A part of the region on the flat face 55 is formed with a metal film 54 made of a material such as Au extending along the widthwise direction. The outer shape of the glass member 55 is identical to that of the wafer 50. Both the groove 55a and the stripe-like opening 51a extend along the widthwise direction. The glass member 55 is disposed on the upper face of the wafer 50 such that one end portion of the groove 55a in the lengthwise direction is located above the lengthwise center position of the stripe-like opening 51a, whereas the other is located above a position away from the tip portion of the NiCr film 53 by a predetermined distance. Then, anode coupling technique is used for joining the glass member 55 and the SiNx film 53 together.

Figure 6A:
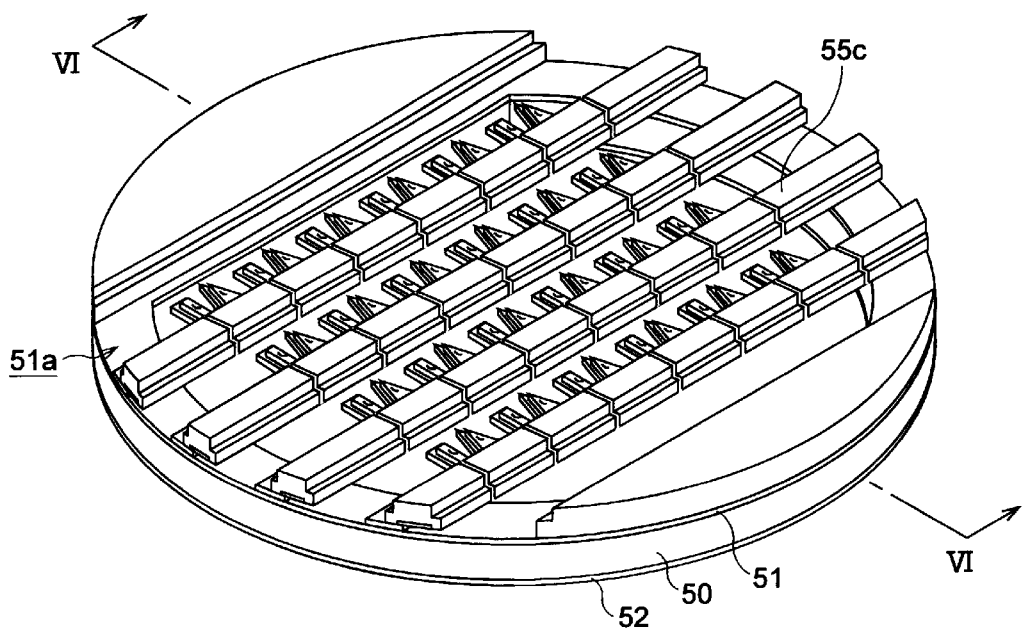
FIG. 6A is a perspective view of a micromechanical sensor intermediate group.
Figure 6B:
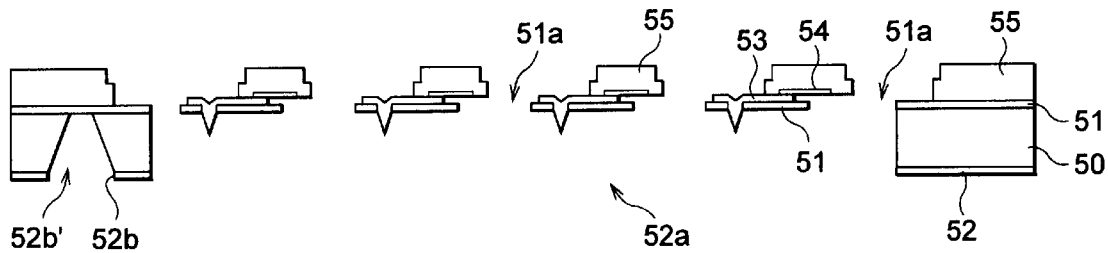
FIG. 6B is a sectional view of the intermediate group shown in FIG. 6A taken along the arrowed line VI—VI.

FIG. 6A is a perspective view of a micromechanical sensor intermediate group, whereas FIG. 6B is a sectional view of the intermediate group shown in FIG. 6A taken along the arrowed line VI—VI. Next, a dicing saw is brought into contact with the glass member 55 on its upper face side along an edge (lengthwise end portion) of the groove 55a defining the widthwise direction thereof. While being rotated, the dicing saw is pushed down till its outer edge exceeds the deepest position of the groove 55a in the glass member 55, thereby separating and removing the area of the glass member 55 formed with the groove 55a from the flat area 55b joined to the wafer 50. Further, grooves 55c for separating devices are formed in the surface of the glass member 55 along the lengthwise direction, thereby making it easier to separate each micromechanical sensor along the groove 55c after a micromechanical sensor group is formed. Further, an etchant for Si, such as KOH, is used for etching the exposed upper and lower faces of the wafer 50 such that the upper-face opening 52a and the lower-face opening 51a communicate with each other, while a plurality of depressed positioning cavities 52b' are formed within the respective plurality of openings 52b.

Figure 7A:
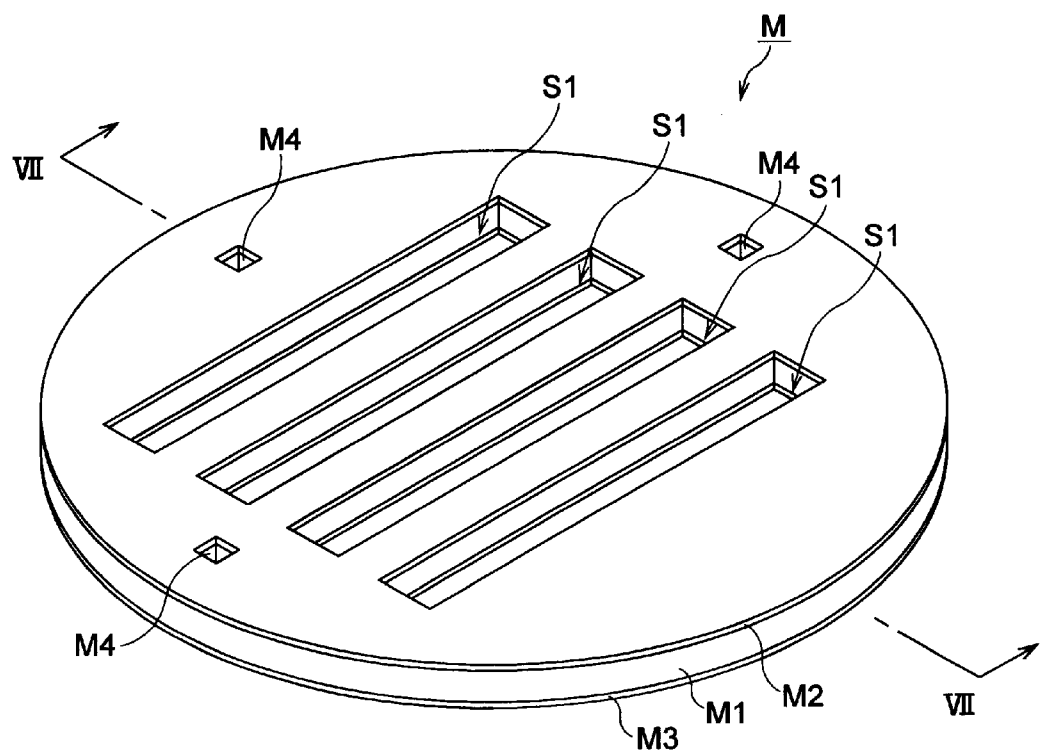
FIG. 7A is a perspective view of a mask M used in the subsequent step.
Figure 7B:
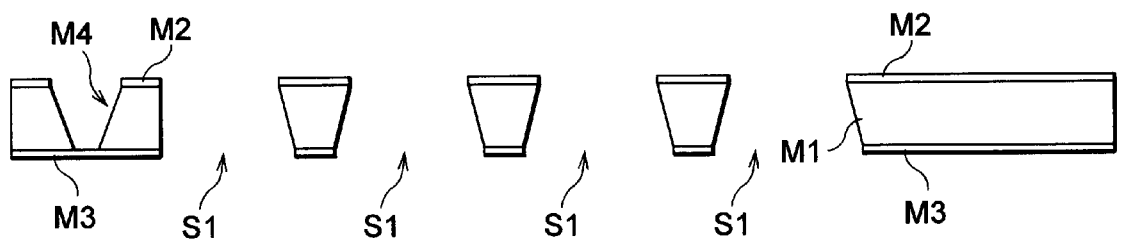
FIG. 7B is a sectional view of the mask shown in FIG. 7A taken along the arrowed line VII—VII.

FIG. 7A is a perspective view of a mask M used for the subsequent step, whereas FIG. 7B is a sectional view of the mask M shown in FIG. 7A taken along the arrowed line VII—VII. The mask M has an outside diameter identical to that of the wafer 50 and is provided with a plurality of stripe-like openings Si formed such as to mask the exposed surface of the metal film 54 in the micromechanical sensor intermediate group. In order to make this mask, first, LPCVD technique is used for forming SiNx films M2 and M3 respectively on the upper and lower faces of an Si wafer M1, a plurality of stripe-like openings are formed in the SiNx films M2 and M3, and then positioning openings are formed in the SiNx film M2. Subsequently, the surface of the Si wafer M1 exposed from within these openings is etched, so as to form stripe-like openings S1 penetrating through the thickness of the Si wafer and extending in the width direction, and positioning cavities M4. The positioning cavity M4 and the cavity 52b' are in mirror symmetry to each other with respect to the surface of the SiNx film M2.

Figure 8A:
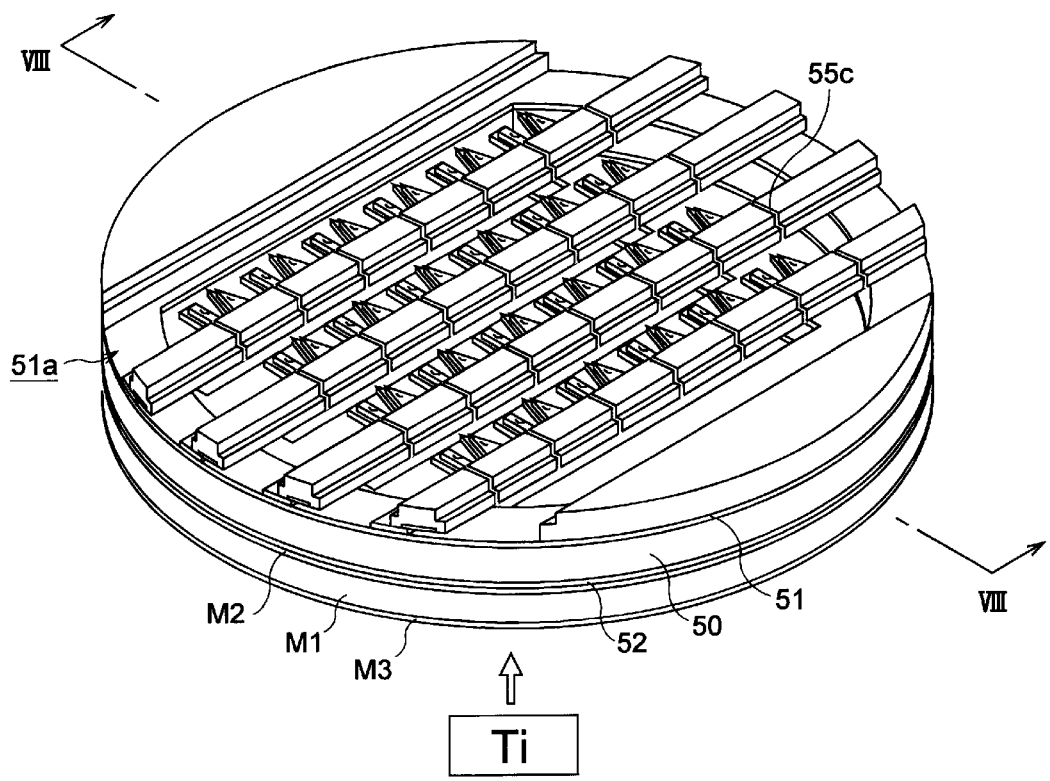
FIG. 8A is a perspective view of a micromechanical sensor intermediate group and a mask.
Figure 8B:
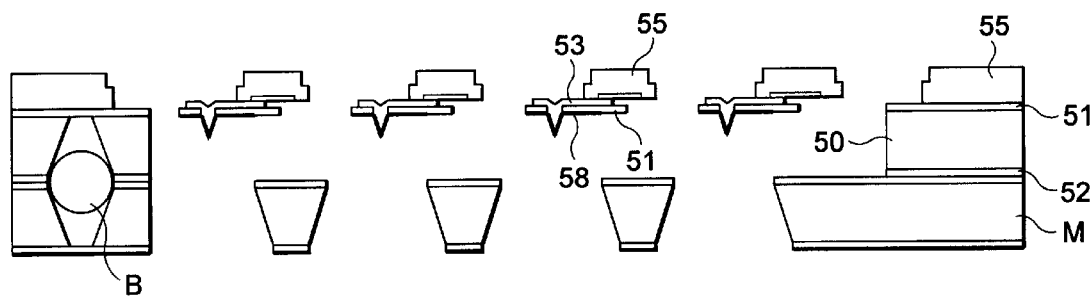
FIG. 8B is a sectional view of the micromechanical sensor intermediate group and mask shown in FIG. 8A taken along the arrowed line VIII—VIII.

FIG. 8A is a perspective view of a micromechanical sensor intermediate group and a mask, whereas FIG. 8B is a sectional view of the micromechanical sensor intermediate group and mask shown in FIG. 8A taken along the arrowed line VIII—VIII. Next, the mask M shown in FIGS. 7A and 7B is disposed under the lower face of the micromechanical sensor intermediate group shown in FIG. 6A. Here, ball bearings B are respectively disposed within a plurality of positioning cavities M4, and the micromechanical sensor intermediate group is disposed such as to position the ball bearings B into the respective cavities 52b. As a consequence, their relative positions are restricted. Though each of the cavities 52b, M4 is formed like a frustum of quadrangular pyramid here, they may have a groove-like form. Also, the bearing B may be shaped like a column or the like as long as it can consequently restrain the relative position between the members. Thereafter, Ti atoms or molecules, which constitute a bonding pad material, are emitted toward the wafer 50 below the mask M, such that the bonding pad material deposits on the SiNx film 52 by way of the mask M, thereby forming a Ti film 58.

Figure 9A:
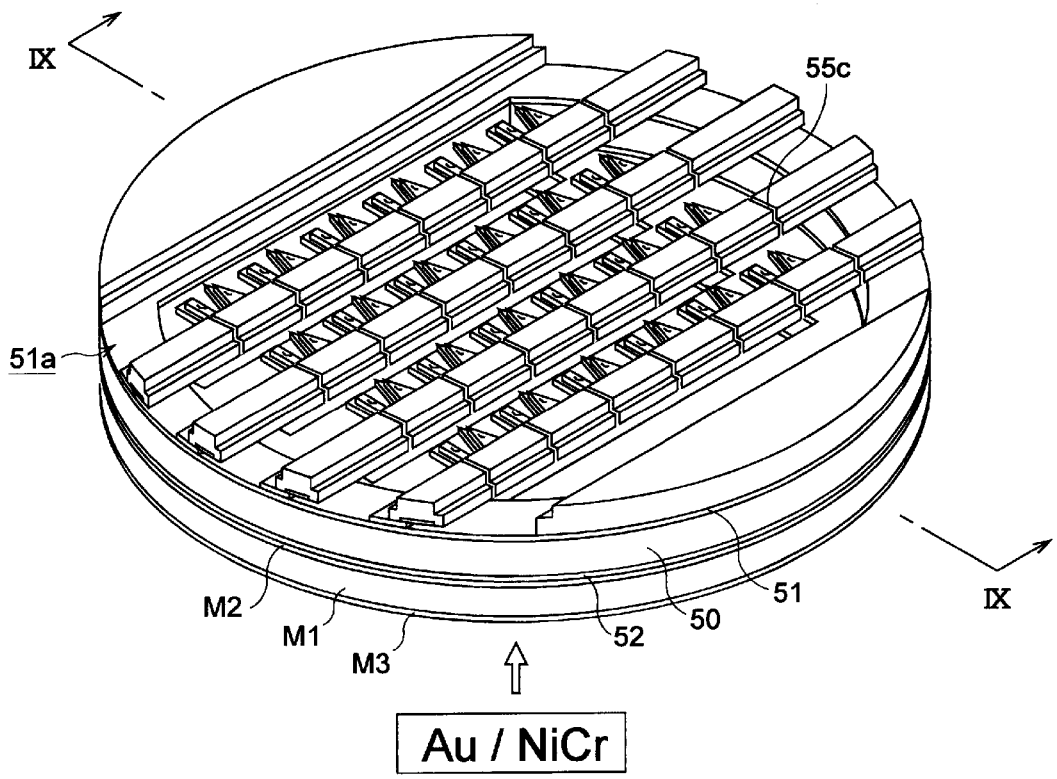
FIG. 9A is a perspective view of a micromechanical sensor intermediate group and a mask.
Figure 9B:
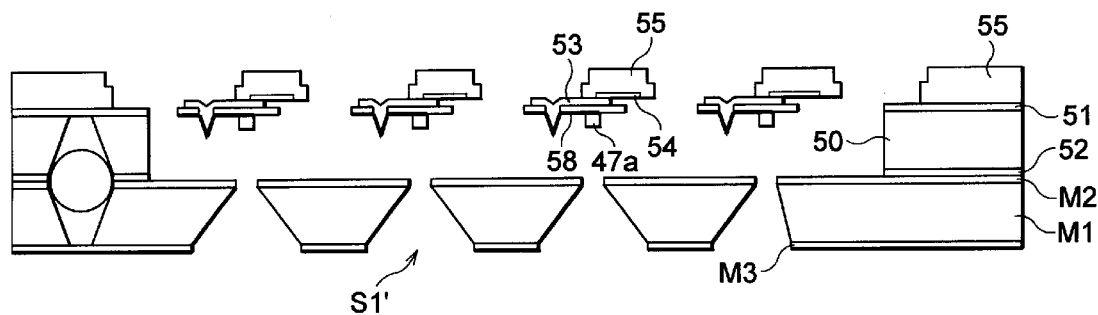
FIG. 9B is a sectional view of the intermediate group shown in FIG. 9A taken along the arrowed line IX—IX.

FIG. 9A is a perspective view of a micromechanical sensor intermediate group and a mask, whereas FIG. 9B is a sectional view of the intermediate group shown in FIG. 9A taken along the arrowed line IX—IX. Next, a mask M' in which only the position and size of stripe-like openings S1' differ from those of the openings Si in the mask M is prepared. The stripe-like opening S1' of the mask M' is formed such as to mask the area other than a part of the Ti film 58 directly below the glass member 55. In the step of forming the Ti film 58, the mask M' is used in place of the mask M, and the depositing material is changed from Ti to Au/NiCr, whereby an Au/NiCr film 47a is formed on the Ti film 58. When an appropriate bonding pad 48a is to be formed on the metal film 54, a similar step is used therefor. As individual devices are separated along the grooves 55c formed in the glass substrate 55, the micromechanical sensor shown in FIG. 1A is accomplished.

Figure 10A:
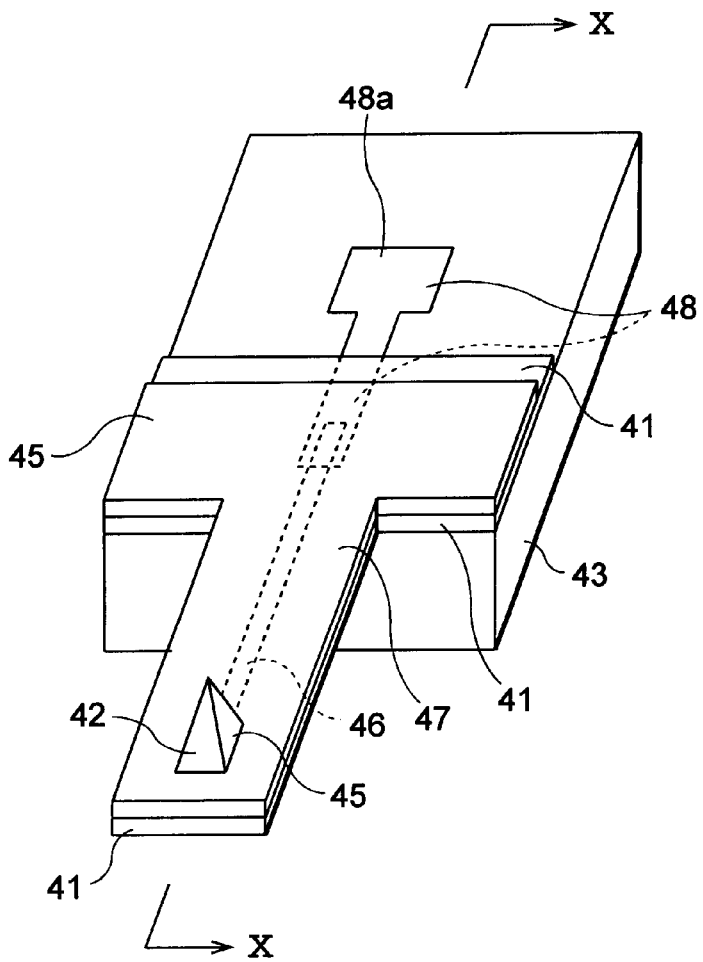
FIG. 10A is a schematic perspective view showing a micromechanical sensor in accordance with another embodiment.
Figure 10B:
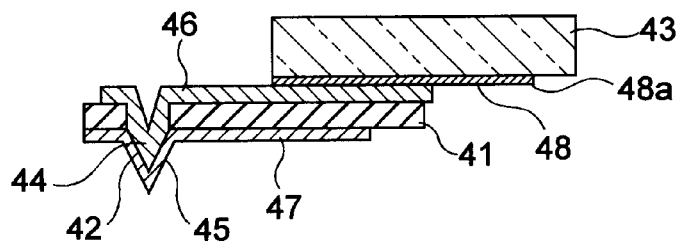
FIG. 10B is a schematic perspective view of the micromechanical sensor shown in FIG. 10A taken along the arrowed line X—X.

FIG. 10A is a schematic perspective view showing a micromechanical sensor in accordance with another embodiment, whereas FIG. 10B is a schematic sectional view of the micromechanical sensor shown in FIG. 10A taken along the arrowed line X—X. Though FIGS. 10A and 10B are depicted in vertically inverted orientations from each other, the vertical orientation is assumed to be based on that of FIG. 10B in the following explanation. Numerals or letters identical to those used in the foregoing will be used, thereby omitting the overlapping explanations. The micromechanical sensor in this embodiment differs from that of the above-mentioned embodiment in that only one cantilever beam is used. This micromechanical sensor is made by use of the method shown in FIGS. 11A to 11E and a method shown in FIGS. 12A to 12F. Also, in the micromechanical sensor explained with reference to FIGS. 12A to 12F, the form of its tip portion 42 differs from that of the above-mentioned embodiment.

An example of method of making the micromechanical sensor shown in FIG. 10A will be explained with reference to FIGS. 11A to 11E. FIGS. 11A to 11E are schematic sectional views showing an example of process for making the micromechanical sensor shown in FIG. 10A.

Figure 11A:
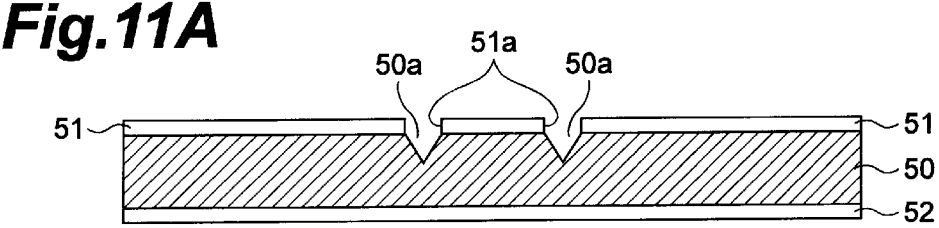
FIGS. 11A, 11B, 11C, 11D, and 11E are schematic sectional views showing an example of process for making the micromechanical sensor shown in FIG. 10A.

First, a silicon substrate 50 of (100) surface orientation having a diameter of 3 inches and a thickness of 250 µm is employed as a substrate material, and silicon nitride films 51, 52 (in which the silicon nitride film 51 corresponds to the flexible plate 41 in FIG. 10A) each having a thickness of 700 nm are respectively formed on both sides of the substrate 50 by LPCVD technique (low pressure CVD technique). Then, lithography technique and dry-etching technique are used for patterning the silicon nitride film 51 on the upper face, such as to form rectangular openings 51a, at predetermined positions of the silicon nitride film 51, for exposing the surface of the substrate 50. In this example, for making a plurality of micromechanical sensors at the same time, the openings 51a are formed so as to correspond in number with the micromechanical sensors to be made at the same time. The pattern form, size, and number of the openings 51a can be set arbitrarily. Subsequently, this substrate is immersed in an etching liquid for silicon, such as aqueous potassium hydroxide (KOH) solution, aqueous tetramethylammonium hydroxide (TMAH) solution, or the like; and, using the silicon nitride films 51, 52 as masks, the part of the substrate exposed from each opening 51a is anisotropically etched so as to form a trench 50a under the opening 51a (FIG. 11A). The trench 50a is formed by silicon (111) faces, thereby yielding a recess shaped like a quadrangular pyramid. In this example, the trench 50a functions as a recess for transferring the form of the probe 42.

Figure 11B:
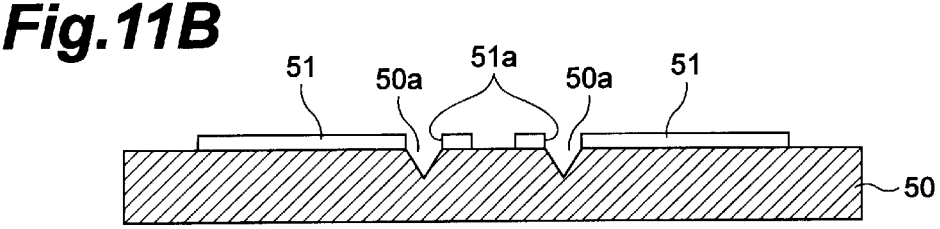

Subsequently, lithography technique and dry-etching technique are used for patterning the silicon nitride film 51 on the upper face in conformity to the form of the flexible plate 41, and removing the silicon nitride film 52 on the lower face (FIG. 11B).

Figure 11C:
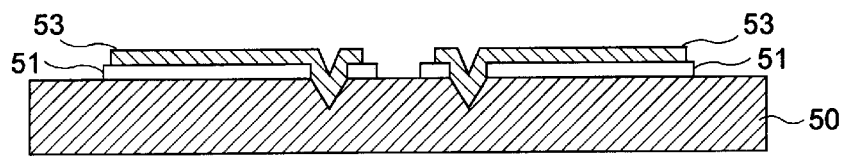

Thereafter, in the area covering the trench 50a and the area corresponding to the wiring conductive film 46, a metal film 53 (corresponding to the metal film 44 in FIG. 10A) is patterned by lift-off technique (FIG. 11C). As the metal film 53, Nichrome can be used, for example.

The step of patterning the silicon nitride film 51 and removing the silicon nitride film 52 explained with reference to FIG. 11B and the step of forming the metal film 53 explained with reference to FIG. 11C may be carried out in the reversed order as well.

Though the foregoing steps constitute a process for preparing the structure shown in FIG. 11C, the process for preparing the latter should not be restricted to such steps.

Figure 11D:
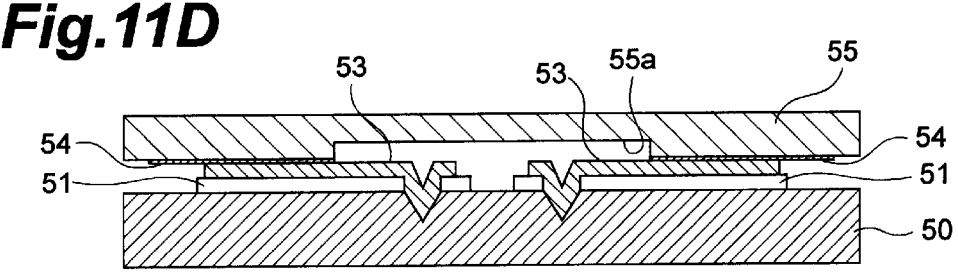

On the other hand, a Pyrex glass member 55 (corresponding to the substrate 43 in FIG. 10A), whose lower face is provided with a metal layer 54 (corresponding to the wiring conductive film 48) made of gold or the like patterned in conformity to the form of the-wiring conductive film 48, is prepared (FIG. 11D). In this embodiment, as the Pyrex glass member 55, a planar member is employed, whose lower face has already been processed by a dicing saw to form grooves 55a for preventing unnecessary parts from being joined together upon anode coupling which will be explained later. In other words, the parts to form the respective substrates 43 of a plurality of micromechanical sensors are cross-linked to each other by the parts formed with the grooves 55a, whereby the Pyrex glass member 55 as a whole has a planar form. Here, the part formed with the groove 55a is provided with separating grooves (not shown).

Then, while the above-mentioned structure and the Pyrex glass member 55 are positioned with respect to each other such that a part of the metal film 53 of the structure shown in FIG. 11C and a part of the metal film 54 of the lower face of the Pyrex glass member 55 overlap and come into contact with each other, the lower face of the Pyrex glass member 55 is joined to the upper face of the silicon nitride film 51 of the structure by anode coupling (FIG. 11D). At this time, a part of the metal film 53 and a part of the metal film 54 are pressed into contact with each other, thereby establishing electric connection therebetween.

Figure 11E:
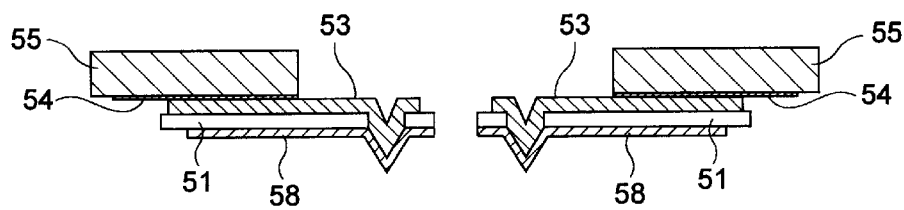

Subsequently, of the Pyrex glass member 55, the part formed with the groove 55a is processed by the dicing saw so as to be cut off. This cutting operation, however, is not effected in the rows-formed with the above-mentioned separating grooves and between end portions of the respective rows. Then, the structure in this state is immersed in the aqueous KOH solution or aqueous TMAH solution, so as to remove the substrate 50. Since the above-mentioned cutting operation is not completely effected, individual micromechanical sensors are still connected to each other in this state (though FIGS. 11A to 11E do not show this connected state). Thereafter, on the probe side of the structure in this state, by using a metal sheet partially having an opening as a masking body, a metal film 58 (corresponding to the metal film 45 in FIG. 10A) made of Ti or the like having a thickness of about 50 nm is partially formed by vapor deposition or the like (FIG. 11E). Finally, the separating grooves are utilized for separating the structure into the individual micromechanical sensors. As a consequence, the micromechanical sensor shown in FIG. 10A is accomplished. The micromechanical sensors in the connected state may be supplied to a measurer, such that the latter can separate the connected assembly into the individual micromechanical sensors by utilizing the separating grooves.

In the micromechanical sensor shown in FIG. 10A, as can be seen from the foregoing explanation, the size and position of the thermocouple are determined by the size and position of the opening 51a in the silicon nitride film 51 formed on the substrate 50. As explained above, the opening 51a can be formed by use of lithography technique (employing an exposure apparatus) and dry-etching technique. As a consequence, the opening 51a can be formed with a very high accuracy in its size and position, and the area thereof can be made very small. Accordingly, the thermocouple can be formed with a very high accuracy in its size and position, and the area thereof can be made very small. As a result, the micromechanical sensor shown in FIG. 10A can yield higher accuracy and resolution when measuring temperature distribution and thermal conductivity distribution in sample surfaces.

Also, in the micromechanical sensor shown in FIG. 10A, the probe 42 and the substrate 43 project from the flexible plate 41 in the directions opposite to each other. Accordingly, upon measurement, corner portions of the substrate 43 would not abut to the sample. Therefore, of the flexible plate 41, the part not joined to the substrate 43 (i.e., lever portion) can be shortened so as to enhance the resonance frequency of the micromechanical sensor, thus allowing high-speed scanning to be realized.

Further, by use of a batch process utilizing a semiconductor manufacturing technique, such as that explained with reference to FIGS. 11A to 11E, the micromechanical sensor shown in FIG. 10A can be mass-produced, so that it can be made available at a low cost.

Another example of method of making the micromechanical sensor shown in FIG. 10A will now be explained with reference to FIGS. 12A to 12F. FIGS. 12A to 12F are schematic sectional views showing another example of process for making the micromechanical sensor shown in FIG. 10A. In FIGS. 12A to 12F, constituents identical or corresponding to those shown in FIGS. 11A to 11E are referred to with numerals or letters identical thereto.

Figure 12A:
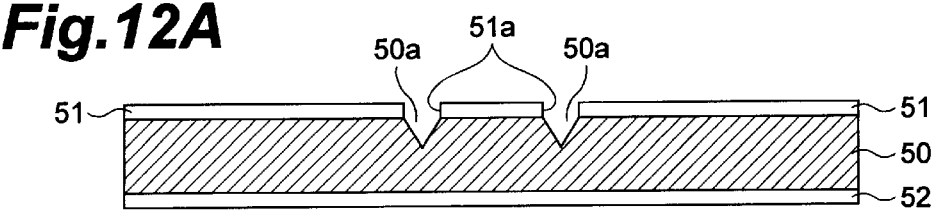
FIGS. 12A, 12B, 12C, 12D, 12E, and 12F are schematic sectional views showing another example of process for making the micromechanical sensor shown in FIG. 10A.

First, a silicon substrate 50 of (100) surface orientation having a diameter of 3 inches and a thickness of 250 μm is employed as a substrate material, and silicon nitride films 51, 52 (in which the silicon nitride film 51 corresponds to the flexible plate 41 in FIG. 10A) each having a thickness of 700 nm are respectively formed on both sides of the substrate 50 by LPCVD technique (low pressure CVD technique). Then, lithography technique and dry-etching technique are used for patterning the silicon nitride film 51 on the upper face, such as to form rectangular openings 51a, at predetermined positions of the silicon nitride film 51, for exposing the surface of the substrate 50. Also in this example, for making a plurality of micromechanical sensors at the same time, the openings 51a are formed so as to correspond in number with the micromechanical sensors to be made at the same time. The pattern form, size, and number of the openings 51a can be set arbitrarily. Subsequently, this substrate is immersed in an etching liquid for silicon, such as aqueous potassium-hydroxide (KOH) solution, aqueous tetramethylammonium hydroxide (TMAH) solution, or the like; and, using the silicon nitride films 51, 52 as masks, the part of the substrate exposed from each opening 51a is anisotropically etched so as to form a trench 50a under the opening 51a (FIG. 12A). The trench 50a is formed by silicon (111) faces, thereby yielding a recess shaped like a quadrangular pyramid.

Figure 12B:
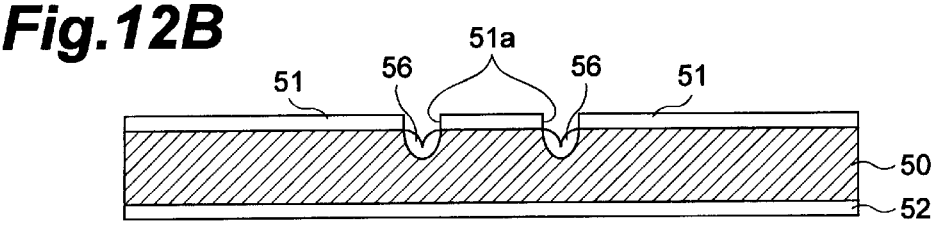

Subsequently, the substrate in the state shown in FIG. 12A is heated in an oxygen atmosphere, such that the inner wall of the trench 50a of the exposed substrate 50 is thermally oxidized (by any type of thermal oxidization such as wet oxidization, dry oxidization, or the like), thereby forming a silicon oxide film 56 (FIG. 12B). Since the oxidization advances slowly in corner portions of a silicone crystal, a steep slope is formed, in particular, near the bottom portion of the trench 50a, i.e., the tip portion of the quadrangular pyramid. In this example, thus steepened trench 50a functions as a recess for transferring the form of the probe 42.

Figure 12C:
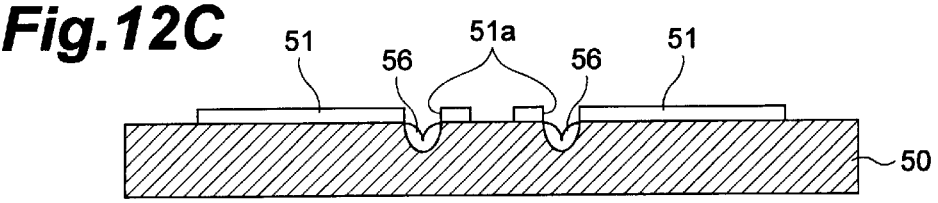

Then, lithography technique and dry-etching technique are used for patterning the silicon nitride film 51 on the upper face in conformity to the form of the flexible plate 41, and removing the silicon nitride film 52 on the lower face (FIG. 12C).

Figure 12D:
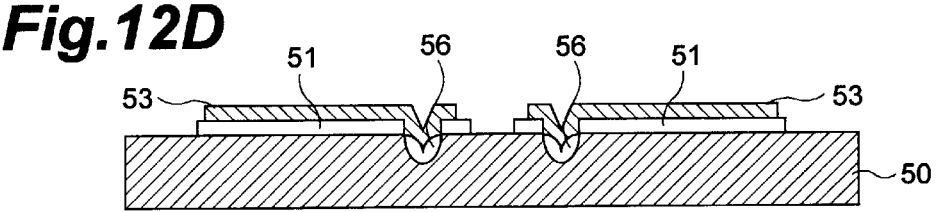

Thereafter, on the substrate in the state shown in FIG. 12C, a metal thin film 53 (corresponding to the metal film 44 in FIG. 10A) is patterned in the area covering the steepened trench 50a and the area corresponding to the wiring conductive film 46 (FIG. 12D).

Though the foregoing steps constitute a process of preparing the structure shown in FIG. 12D, the process of preparing the latter should not be restricted to such steps.

Figure 12E:
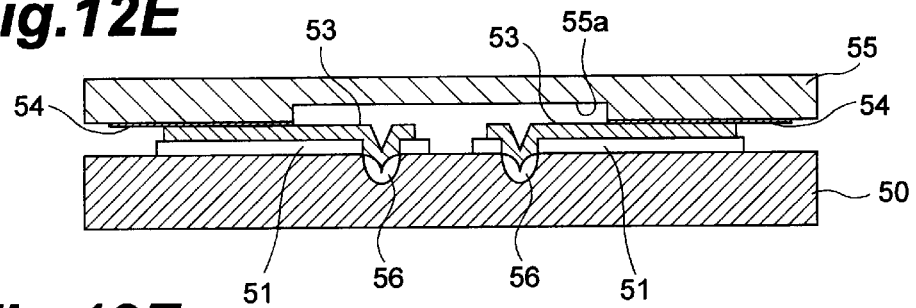

On the other hand, a Pyrex glass member 55 (corresponding to the substrate 43 in FIG. 10A), whose lower face is provided with a metal layer 54 (corresponding to the wiring conductive film 48) made of gold or the like patterned in conformity to the form of the wiring conductive film 48, is prepared (FIG. 12E). In this embodiment, as the Pyrex glass member 55, a planar member is employed, whose lower face has already been processed by a dicing saw to form grooves 55a for preventing unnecessary parts from being joined together upon anode coupling which will be explained later. In other words, the parts to form the respective substrates 43 of a plurality of micromechanical sensors are cross-linked to each other by the parts formed with the grooves 55a, whereby the Pyrex glass member 55 as a whole has a planar form. Here, the part formed with the groove 55a is provided with separating grooves (not shown).

Then, while the above-mentioned structure and the Pyrex glass member 55 are positioned with respect to each other such that a part of the metal film 53 of the structure shown in FIG. 12D and a part of the metal film 54 of the lower face of the Pyrex glass member 55 overlap and come into contact with each other, the lower face of the Pyrex glass member 55 is joined to the upper face of the silicon nitride film 51 of the structure by anode coupling (FIG. 12E). At this time, a part of the metal film 53 and a part of the metal film 54 are pressed into contact with each other, thereby establishing electric connection therebetween.

Figure 12F:
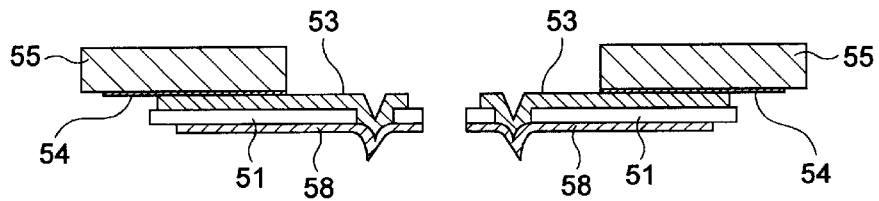

Subsequently, of the Pyrex glass member 55, the part formed with the groove 55a is processed by the dicing saw so as to be cut off. This cutting operation, however, is not effected in the rows formed with the above-mentioned separating grooves and between end portions of the respective rows. Then, the structure in this state is immersed in the aqueous KOH solution or aqueous TMAH solution, so as to remove the substrate 50 and the silicon oxide film 56. Since the above-mentioned cutting operation is not completely effected, individual micromechanical sensors are still connected to each other in this state (though FIGS. 12A to 12E do not show this connected state). Thereafter, on the probe side of the structure in this state, by using a metal sheet partially having an opening as a masking body, a metal film 58 (corresponding to the metal film 45 in FIG. 10A) made of Ti or the like having a thickness of about 50 nm is partially formed by vapor deposition or the like (FIG. 12F). Finally, the separating grooves are utilized for separating the structure into the individual micromechanical sensors. As a consequence, the micromechanical sensor shown in FIG. 10A is accomplished. The micromechanical sensors in the connected state may be supplied to a measurer, such that the latter can separate the connected assembly into the individual micromechanical sensors by utilizing the separating grooves.

In the micromechanical sensor obtained by the method explained with reference to FIGS. 12A to 12F, since the recess for transferring the form of the probe 42 becomes the steepened trench 50a, the tip portion of the probe 42 becomes steeper than that in the micromechanical sensor made by the method explained with reference to FIGS. 11A to 11E, thus improving the resolution in measurement.

In the following, a micromechanical sensor in accordance with another embodiment will be explained with reference to FIGS. 13A and 13B. The micromechanical sensor in accordance with this embodiment is also configured as a micromechanical sensor for a microscope achieving functions of both scanning heat measurement microscope and scanning atomic force microscope.

Figure 13A:
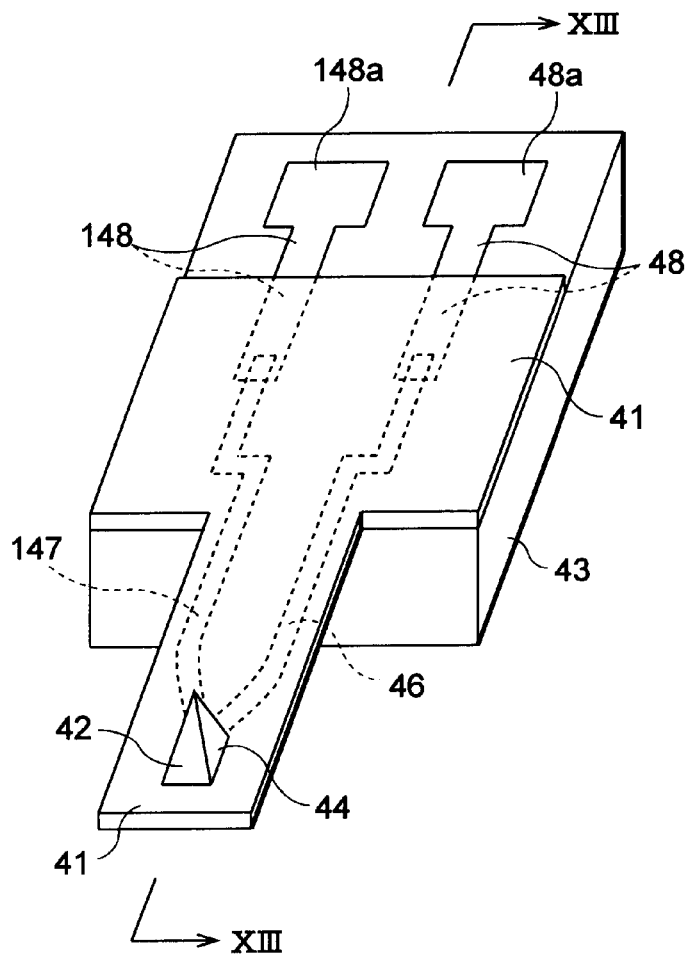
FIG. 13A is a schematic perspective view showing a micromechanical sensor in accordance with an embodiment.
Figure 13B:
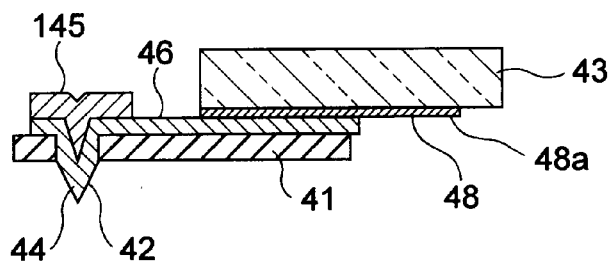
FIG. 13B is a schematic perspective view of the micromechanical sensor shown in FIG. 13A taken along the arrowed line XIII—XIII.

FIG. 13A is a schematic perspective view showing a micromechanical sensor in accordance with this embodiment, whereas FIG. 13B is a schematic sectional view of the micromechanical sensor shown in FIG. 13A taken along the arrowed line XIII—XIII. Though FIGS. 13A and 13B are depicted in vertically inverted orientations from each other, the vertical orientation is assumed to be based on that of FIG. 13B in the following explanation. The constituents in FIGS. 13A and 13B identical to or corresponding to those in FIG. 10A will be referred to with numerals or letters identical thereto, without repeating their overlapping explanations.

The micromechanical sensor in this embodiment differs from that shown in FIG. 10A in the following points.

In this embodiment, the metal film 45 (together with the wiring conductive film 47 as a consequence) in FIG. 10A is removed, whereas a metal film 145 of a kind different from the metal film 44, a wiring conductive film 147, and a wiring conductive film 148 are additionally used instead.

Namely, the probe 42 is constituted by the metal film 44 and the metal film 145 formed on the metal film 44, whereas the joint between the metal films 44, 145 in the probe 42 forms a thermocouple. The metal film 145 overlaps with the metal film 44 only where the probe 42 is located. The metal film 145 is formed on the upper face (surface facing the substrate 43) of the flexible plate 41, continuously from the thermocouple portion. The upper face of the flexible plate 41 is formed with the wiring conductive film 147, which is electrically connected to the metal film 145 and extends over the proximal end side area of the flexible plate 41. In this embodiment, the wiring conductive film 147 is formed as a direct extension of the metal film 145. The wiring conductive film 147, however, may also be made of a metal material different from that of the metal film 145, a plurality films patched together, or a multilayer film.

The lower face (surface facing the flexible plate 41) of the substrate 43 is formed with a wiring conductive film 148, made of a metal film, extending from an area overlapping with the flexible plate 41 to an area not overlapping with the flexible plate 41. An end portion of the wiring conductive film 148 in the non-overlapping area constitutes an electrode pad portion 148a for electric connection with the outside. In this embodiment, the wiring conductive film 148 constitutes a conductor for external connection, a part of which is disposed so as to electrically connect with the wiring conductive film 147, while another part is lead to the outside. A conductor such as metal foil, wire, or the like may also be used as the conductor for external connection, though.

The flexible plate 41 and the substrate 43 are joined together such that the wiring conductive film 147 and the wiring conductive film 148 are electrically connected to each other. In this embodiment, the substrate 43 is made of a glass material (e.g., borosilicate glass) containing a movable ion, and the flexible plate 41 and the substrate 43 are joined together by anode coupling. Nevertheless, the substrate 43 may also be made of other insulating materials, and the joint between the flexible plate 41 and the substrate 43 is not always restricted to anode coupling.

An example of method of making the micromechanical sensor shown in FIGS. 13A and 13B will be explained with reference to FIGS. 14A to 14E. FIGS. 14A to 14E are schematic sectional views showing an example of process for making the micromechanical sensor shown in FIGS. 13A and 13B. In FIGS. 14A to 14E, constituents identical or corresponding to those in FIGS. 11A to 11E are referred to with numerals or letters identical thereto.

Figure 14A:
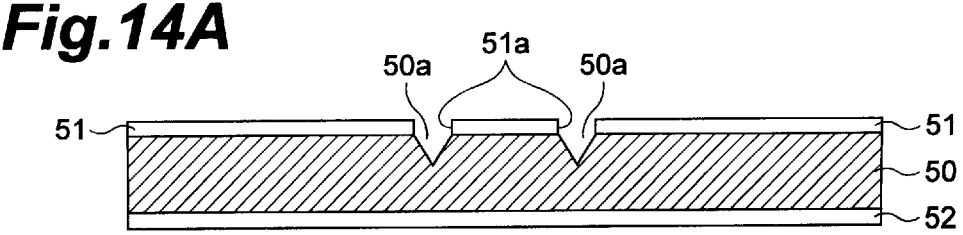
FIGS. 14A, 14B, 14C, 14D, and 14E are schematic sectional views showing an example of process for making the micromechanical sensor shown in FIGS. 13A and 13B.

First, a silicon substrate 50 of (100) surface orientation having a diameter of 3 inches and a thickness of 250 μm is employed as a substrate material, and silicon nitride films 51, 52 (in which the silicon nitride film 51 corresponds to the flexible plate 41 in FIGS. 13A) each having a thickness of 700 nm are respectively formed on both sides of the substrate 50 by LPCVD technique (low pressure CVD technique). Then, lithography technique and dry-etching technique are used for patterning the silicon nitride film 51 on the upper face, such as to form rectangular openings 51a, at predetermined positions of the silicon nitride film 51, for exposing the surface of the substrate 50. In this example, for making a plurality of micromechanical sensors at the same time, the openings 51a are formed so as to correspond in number with the micromechanical sensors to be made at the same time. The pattern form, size, and number of the openings 51a can be set arbitrarily. Subsequently, this substrate is immersed in an etching liquid for silicon, such as aqueous potassium hydroxide (KOH) solution, aqueous tetramethylammonium hydroxide (TMAH) solution, or the like; and, using the silicon nitride films 51, 52 as masks, the part of the substrate exposed from each opening 51a is anisotropically etched so as to form a trench 50a under the opening 51a (FIG. 14A). The trench 50a is formed by silicon (111) faces, thereby yielding a recess shaped like a quadrangular pyramid. In this example, the trench 50a functions as a recess for transferring the form of the probe 42.

Figure 14B:
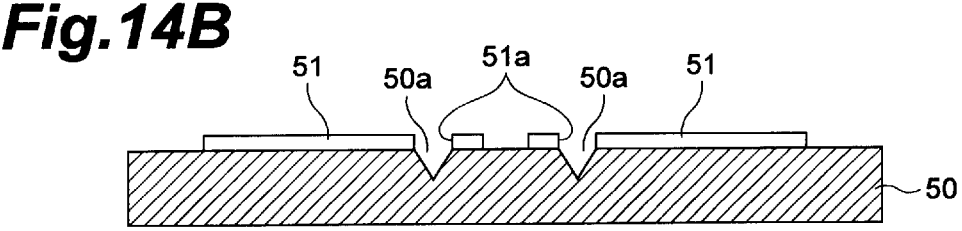

Subsequently, lithography technique and dry-etching technique are used for patterning the silicon nitride film 51 on the upper face in conformity to the form of the flexible plate 41, and removing the silicon nitride film 52 on the lower face (FIG. 14B).

Thereafter, on the substrate in the state shown in FIG. 14B, in the area covering the trench 50a and the area corresponding to the wiring conductive film 46, a metal film 53 such as Nichrome (NiCr) or the like (corresponding to the metal film 44 in FIG. 13A) is patterned by lift-off technique. Subsequently, on the substrate in the resulting state, in the area of the trench 50a overlapping with the metal film 53 and the area corresponding to the wiring conductive film 147 extending from the overlapping area onto the silicon nitride film 51, a metal film 245 such as Ti-(corresponding to the metal film 145 in FIG. 13A) is patterned by lift-off technique (FIG. 14C).

Figure 14C:
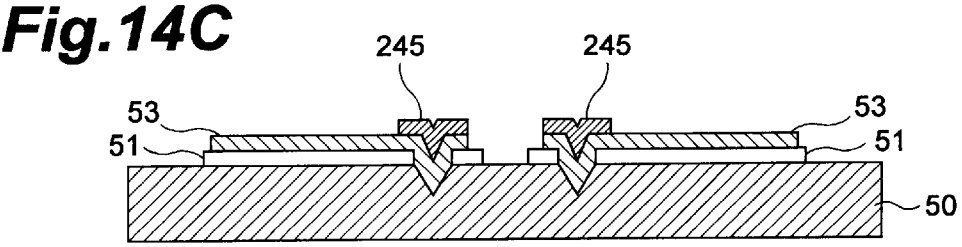

Though the foregoing steps constitute a process of preparing the structure shown in FIG. 14C, the process of preparing the latter should not be restricted thereto.

Figure 14D:
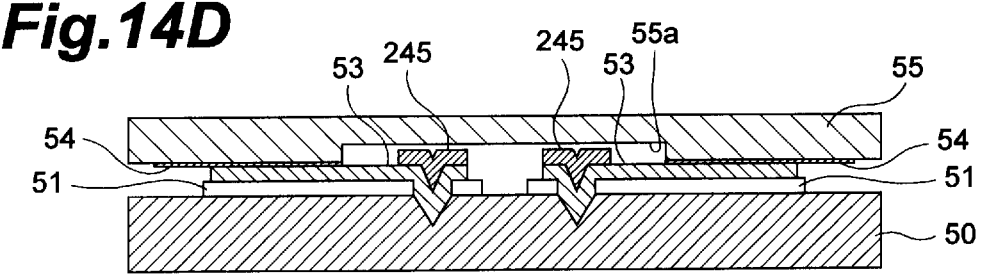
Figure 14E:
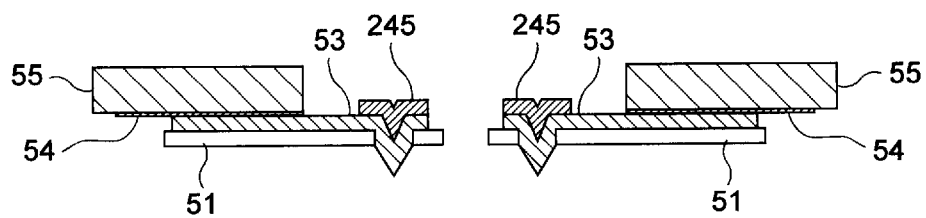

On the other hand, a Pyrex glass member 55 (corresponding to the substrate 43 in FIG. 13A), whose lower face is provided with a metal layer 54 (corresponding to the wiring conductive films 48, 148) made of gold or the like patterned in conformity to the form of the wiring conductive films 48, 148 is prepared (FIG. 14D). In this embodiment, as the Pyrex glass member 55, a planar member is employed, whose lower face has already been processed by a dicing saw to form grooves 55a for preventing unnecessary parts from being joined together upon anode coupling which will be explained later. In other words, the parts to form the respective substrates 43 of a plurality of micromechanical sensors are cross-linked to each other by the parts formed with the grooves 55a, whereby the Pyrex glass member 55 as a whole has a planar form. Here, the part formed with the groove 55a is provided with separating grooves (not shown).

Then, the above-mentioned structure and the Pyrex glass member 55 are positioned with respect to each other such that a part of the metal film 53 of the structure shown in FIG. 14C and a part of the metal film 54 of the lower face of the Pyrex glass member 55 overlap and come into contact with each other, while a part of the metal film 245 of the structure shown in FIG. 14C and another part of the metal film 54 of the lower face of the Pyrex glass member 55 overlap and come into contact with each other; and the lower face of the Pyrex glass member 55 is joined to the upper face of the silicon nitride film 51 of the structure by anode coupling (FIG. 14D). At this time, a part of the metal film 53 and a part of the metal film 54 are pressed into contact with each other so as to establish electric connection therebetween, whereas a part of the metal film 245 and another part of the metal film 54 are pressed into contact with each other so as to establish electric connection therebetween.

Subsequently, of the Pyrex glass member 55, the part formed with the groove 55a is processed by the dicing saw so as to be cut off. This cutting operation, however, is not effected in the rows formed with the above-mentioned separating grooves and between end portions of the respective rows. Then, the structure in this state is immersed in the aqueous KOH solution or aqueous TMAH solution, so as to remove the substrate 50. Since the above-mentioned cutting operation is not completely effected, individual micromechanical sensors are still connected to each other in this state (though FIGS. 14A to 14E do not show this connected state). Finally, the separating grooves are utilized for separating the structure into the individual micromechanical sensors. As a consequence, the micromechanical sensor shown in FIG. 13A is accomplished. The micromechanical sensors in the connected state may be supplied to a measurer, such that the latter can separate the connected assembly into the individual micromechanical sensors by utilizing the separating grooves.

In the micromechanical sensor shown in FIG. 13A, as can be seen from the foregoing explanation, a film-forming technique with a high accuracy using an exposure apparatus, such as lift-off technique, can be employed in order to form metal films 46, 145 (i.e., metal films 53, 245), whereby their overlapping portions, i.e., the size and position of the thermocouple can be set with a very high accuracy, and the area thereof can be made very small. Accordingly, the thermocouple can be formed with a very high accuracy in its size and position, and with a very small area. As a result, the micromechanical sensor shown in FIG. 13A can yield higher accuracy and resolution when measuring temperature distribution and thermal conductivity distribution in sample surfaces.

Also, in the micromechanical sensor shown in FIG. 13A, the probe 42 and the substrate 43 project from the flexible plate 41 in the directions opposite to each other. Accordingly, upon measurement, corner portions of the substrate 43 would not abut to the sample. Therefore, of the flexible plate 41, the part not joined to the substrate 43 (i.e., lever portion) can be shortened so as to increase the resonance frequency of the micromechanical sensor, thus allowing high-speed scanning to be realized.

Further, by use of a batch process utilizing a semiconductor manufacturing technique, such as that explained with reference to FIGS. 14A to 14E, the micromechanical sensor shown in FIG. 13A can be mass-produced, so that it can be made available at a low cost.

Another example of method of making the micromechanical sensor shown in FIG. 13A will now be explained with reference to FIGS. 15A to 15F. FIGS. 15A to 15F are schematic sectional views showing another example of process for making the micromechanical sensor shown in FIG. 13A. In FIGS. 15A to 15F, constituents identical or corresponding to those shown in FIGS. 14A to 14E are referred to with numerals or letters identical thereto.

First, a silicon substrate 50 of (100) surface orientation having a diameter of 3 inches and a thickness of 250 µm is employed as a substrate material, and silicon nitride films 51, 52 (in which the silicon nitride film 51 corresponds to the flexible plate 41 in FIG. 13A) each having a thickness of 700 nm are respectively formed on both sides of the substrate 50 by LPCVD technique (low pressure CVD technique). Then, lithography technique and dry-etching technique are used for patterning the silicon nitride film 51 on the upper face, such as to form rectangular openings 51a, at predetermined positions of the silicon nitride film 51, for exposing the surface of the substrate 50. Also in this example, for making a plurality of micromechanical sensors at the same time, the openings 51a are formed so as to correspond in number with the micromechanical sensors to be made at the same time. The pattern form, size, and number of the openings 51a can be set arbitrarily. Subsequently, this substrate is immersed in an etching liquid for silicon, such as aqueous potassium hydroxide (KOH) solution, aqueous tetramethylammonium hydroxide (TMAH) solution, or the like; and, using the silicon-nitride films 51, 52 as masks, the part of the substrate exposed from each opening 51a is anisotropically etched so as to form a trench 50a under the opening 51a (FIG. 15A). The trench 50a is formed by silicon (111) faces, thereby yielding a recess shaped like a quadrangular pyramid.

Subsequently, the substrate in the state shown in FIG. 15A is heated in an oxygen atmosphere, such that the inner wall of the trench 50a of the exposed substrate 50 is thermally oxidized (by any type of thermal oxidization such as wet oxidization, dry oxidization, or the like), thereby forming a silicon oxide film 56 (FIG. 15B). Since the oxidization advances slowly in corner portions of a silicone crystal, a steep slope is formed, in particular, near the bottom portion of the trench 50a, i.e., the tip portion of the quadrangular pyramid. In this example, thus steepened trench 50a functions as a recess for transferring the form of the probe 42.

Then, lithography technique and dry-etching technique are used for patterning the silicon nitride film 51 on the upper face in conformity to the form of the flexible plate 41, and removing the silicon nitride film 52 on the lower face (FIG. 15C).

Thereafter, on the substrate in the state shown in FIG. 15C, a metal thin film 53 such as Nichrome (NiCr) or the like (corresponding to the metal film 44 in FIG. 13A) is patterned in the area covering the steepened trench 50a and the area corresponding to the wiring conductive film 46 by lift-off technique. Then, on the substrate in the resulting state, in the area overlapping with the metal film 53 in thus steepened trench 50a and the area corresponding to the wiring conductive film 147 extending from the overlapping area onto the silicon nitride film 51, a metal film 245 such as Ti or the like (corresponding to the metal film 145 in FIG. 13A) is patterned by lift-off technique (FIG. 15D).

Though the foregoing steps constitute a process of preparing the structure shown in FIG. 15D, the process of preparing the latter should not be restricted to such steps.

On the other hand, a Pyrex glass member 55 (corresponding to the substrate 43 in FIG. 13A), whose lower face is provided with a metal layer 54 (corresponding to the wiring conductive films 48, 148) made of gold or the like patterned in conformity to the form of the wiring conductive films 48, 148, is prepared (FIG. 15E). In this embodiment, as the Pyrex glass member 55, a planar member is employed, whose lower face has already been processed by a dicing saw to form grooves 55a for preventing unnecessary parts from being joined together upon anode coupling which will be explained later. In other words, the parts to form the respective substrates 43 of a plurality of micromechanical sensors are cross-linked to each other by the parts formed with the grooves 55a, whereby the Pyrex glass member 55 as a whole has a planar form. Here, the part formed with the groove 55a is provided with separating grooves (not shown).

Then, the above-mentioned structure and the Pyrex glass member 55 are positioned with respect to each other such that a part of the metal film 53 of the structure shown in FIG. 15D and a part of the metal film 54 of the lower face of the Pyrex glass member 55 overlap and come into contact with each other, while a part of the metal film 245 of the structure shown in FIG. 15D and another part of the metal film 54 of the lower face of the Pyrex glass member 55 overlap and come into contact with each other; and the lower face of the Pyrex glass member 55 is joined to the upper face of the silicon nitride film 51 of the structure by anode coupling (FIG. 15E). At this time, a part of the metal film 53 and a part of the metal film 54 are pressed into contact with each other so as to establish electric connection therebetween, whereas a part of the metal film 245 and another part of the metal film 54 are pressed into contact with each other so as to establish electric connection therebetween.

Subsequently, of the Pyrex glass member 55, the part formed with the groove 55a is processed by the dicing saw so as to be cut off (FIG. 15F). This cutting operation, however, is not effected in the rows formed with the above-mentioned separating grooves and between end portions of the respective rows. Then, the structure in this state is immersed in the aqueous KOH solution or aqueous TMAH solution, so as to remove the substrate 50. Since the above-mentioned cutting operation is not completely effected, individual micromechanical sensors are still connected to each other in this state (though FIGS. 15A to 15F do not show this connected state). Finally, the separating grooves are utilized for separating the structure into the individual micromechanical sensors. As a consequence, the micromechanical sensor shown in FIG. 13A is accomplished. The micromechanical sensors in the connected state may be supplied to a measurer, such that the latter can separate the connected assembly into the individual micromechanical sensors by utilizing the separating grooves.

In the micromechanical sensor obtained by the method explained with reference to FIGS. 15A to 15F, since the recess for transferring the form of the probe 42 becomes the steepened trench 50a, the tip portion of the probe 42 becomes steeper than that in the micromechanical sensor made by the method explained with reference to FIGS. 14A to 14E, thus improving the resolution in measurement.

Figure 16A:
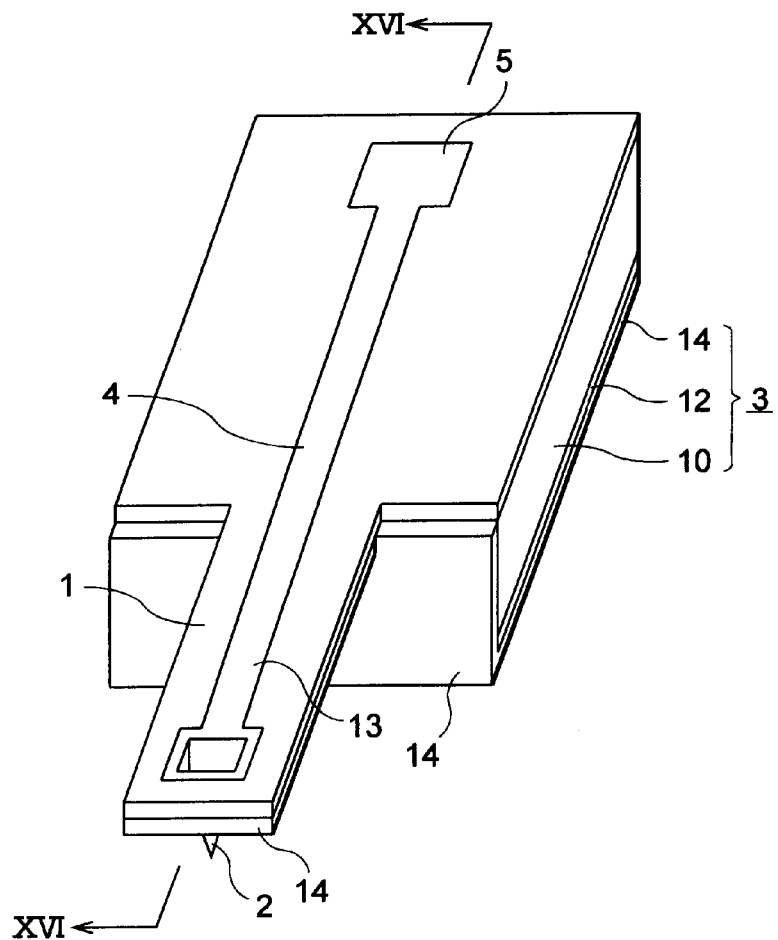
FIG. 16A is a schematic perspective view showing a micromechanical sensor.
Figure 16B:
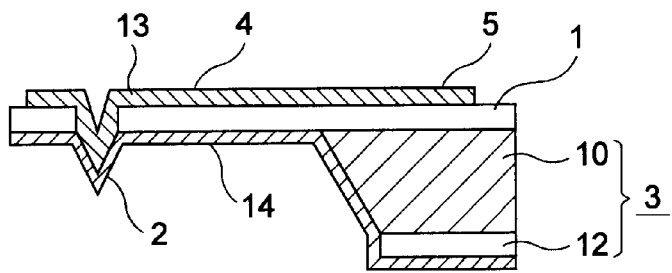
FIG. 16B is a schematic sectional view of the micromechanical sensor shown in FIG. 16A taken along the arrowed line XVI—XVI.

FIGS. 16A and 16B show an example of micromechanical sensor used in a scanning thermal imaging microscope. FIG. 16A is a schematic perspective view showing the micromechanical sensor, whereas FIG. 16B is a schematic sectional view of the micromechanical sensor in FIG. 16A taken along the arrowed line XVI—XVI.

This micromechanical sensor comprises a flexible, plate 1 made of a silicon nitride film as an insulating material, a probe 2 projecting from the lower face of the flexible plate 1 in its tip side area, and a substrate joined to the lower face of the flexible plate 1 in its proximal end side area. Accordingly, the probe 2 and the substrate 3 project from the flexible plate 1 in the same direction. The probe 2 is constituted by metal films 13, 14 of kinds different from each other, and the joint between the metal films 13, 14 in the probe 12 constitutes a thermocouple. The metal film 13 projects downward from an opening formed at the part of the flexible plate 1 corresponding to the probe 2. The substrate 3 is constituted by a silicon layer 10 and a silicon nitride film 12 formed on the lower face of the silicon layer 10. On the upper face of the flexible plate 1, a wiring conductive layer 4 made of the metal film 13 continuing from the thermocouple portion of the probe 2 is formed so as to extend over the proximal end side area. Formed on the proximal end side area of the flexible plate 1 is an electrode pattern (pad portion) 5, made of the metal film 13 continuous with the wiring conductive film 4, for electric connection with the outside. The metal film 14 is formed all over the flexible plate 1, the metal film 13 projecting from the opening of the flexible plate 1, and the lower face of the substrate 3.

The micromechanical sensor shown in FIG. 16A is made by a method such as that explained in the following. FIGS. 17A to 17E are schematic views showing an example of process for making the micromechanical sensor shown in FIG. 16A.

Figure 17A:
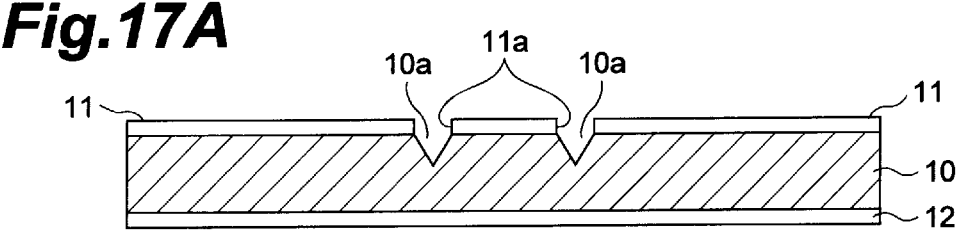
FIGS. 17A, 17B, 17C, 17D, and 17E are schematic sectional views showing an example of process for making the micromechanical sensor shown in FIG. 16A.
Figure 17B:
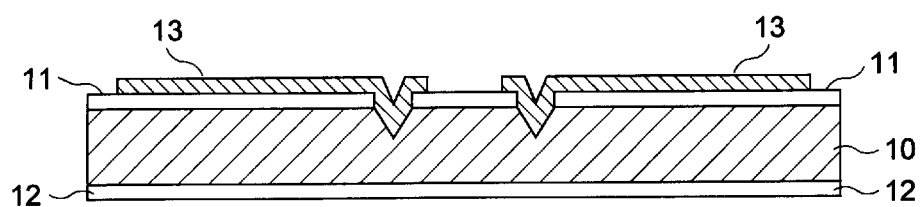

First, a silicon substrate 10 of (100) surface orientation is prepared; and silicon nitride films 11, 12, which become materials for the flexible plate 1, are respectively formed on both sides of the substrate 10. Subsequently, lithography technique and dry-etching technique are used for patterning the silicon nitride film 11 on the upper face, so as to form rectangular openings 11a, at predetermined positions, for exposing the surface of the substrate 10. Thereafter, the part of the substrate 10 exposed from each opening 11a is anisotropically etched by wet etching, such that a trench 10a shaped like a quadrangular pyramid is formed under the opening 11a (FIG. 17A). Then, on the substrate in the state shown in FIG. 17A, by lift-off technique, the metal film 13 is patterned over the area covering the trench 10a, the area corresponding to the wiring conductive film 4, and the area corresponding to the electrode pattern 5 (FIG. 17B).

Figure 17C:
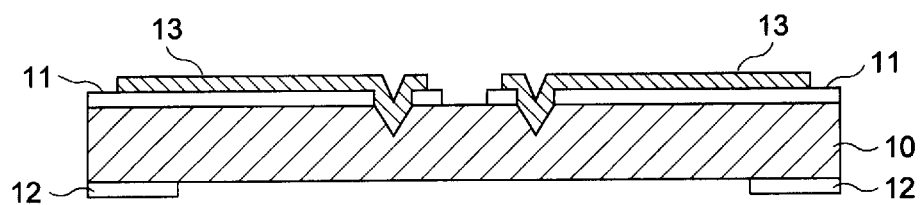
Figure 17D:
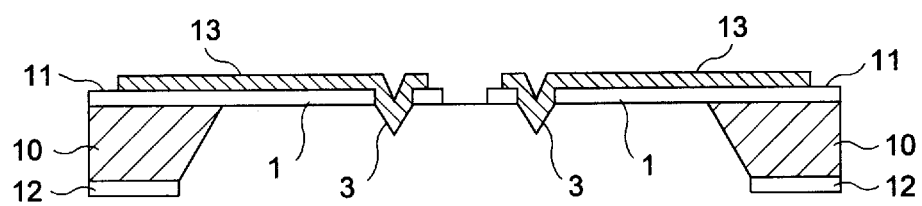
Figure 17E:
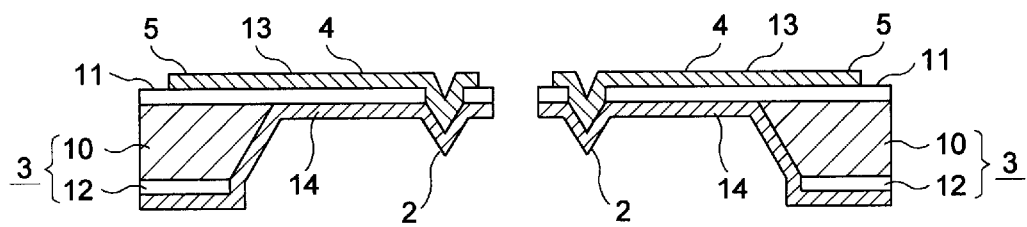

Subsequently, lithography technique and dry-etching technique are used for patterning the silicon nitride film 11 on the upper face in conformity to the form of the flexible plate 1, and patterning the silicon nitride film 12 on the lower face in conformity to the form of the substrate 3 (FIG. 17C). Then, the substrate in the state shown in FIG. 17C is immersed in an aqueous KOH solution, so as to dissolve and remove the silicon portion of the exposed substrate 10 (FIG. 17D). Finally, on the whole lower face of the structure in the state shown in FIG. 17D, a metal film 14 made of a material different from that of the metal film 13 is formed (FIG. 17E). As a consequence, the micromechanical sensor shown in FIG. 16A is accomplished. According to this method, the silicon nitride film 11 constitutes the flexible plate 1, whereas the remaining substrate 10 and silicon nitride film 12 constitute the substrate 3.

Figure 18A:
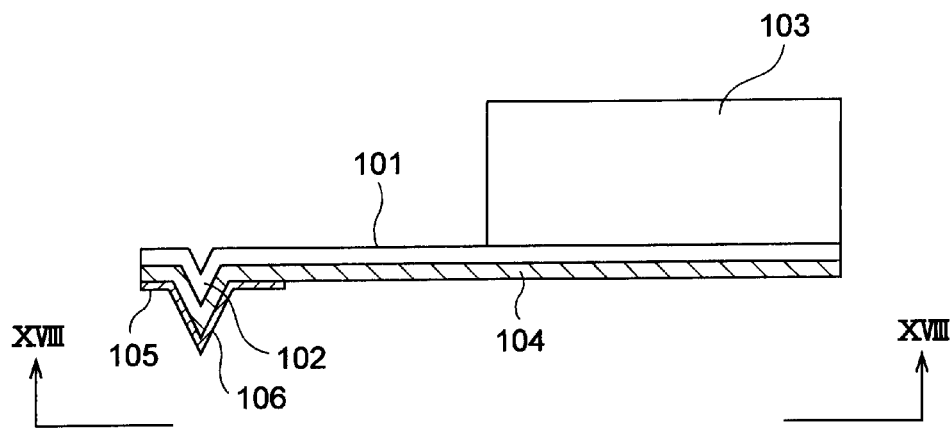
FIG. 18A is a schematic sectional view showing a micromechanical sensor.
Figure 18B:
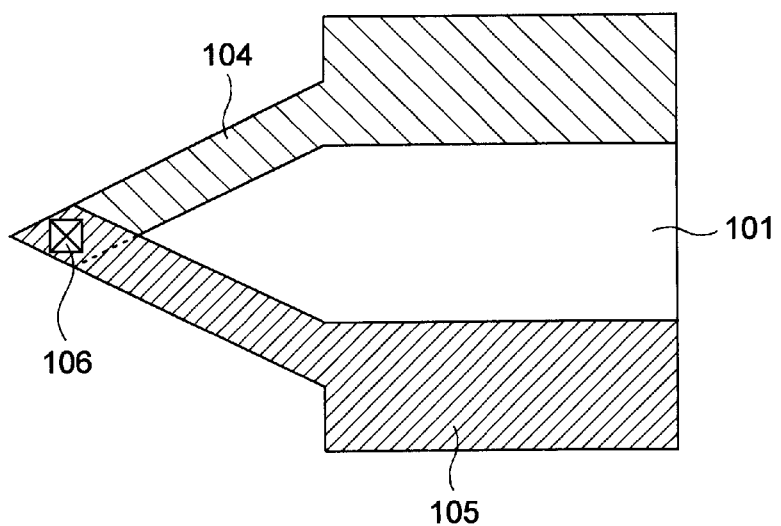
FIG. 18B is a schematic plan view of the micromechanical sensor shown in FIG. 18A taken along the arrowed line XVIII—XVIII.

FIGS. 18A and 18B show another example of micromechanical sensor used in an atomic force thermal imaging microscope. FIG. 18A is a schematic perspective view showing the micromechanical sensor, whereas FIG. 18B is a schematic sectional view of the micromechanical sensor in FIG. 18A taken along the arrowed line XVIII—XVIII.

This micromechanical sensor, used for an atomic force microscope, is constituted by a flexible plate 101 and a probe 102 (projecting from the lower face of the flexible plate 101 in its tip side area) which are integrally formed by a silicon nitride film, and a substrate 103 made of a glass member joined to the upper face of the flexible plate 101 in its proximal end side area. In the micromechanical sensor shown in FIGS. 18A and 18B, on the surface of the micromechanical sensor for the atomic force microscope on the probe 102 side, different kinds of metal films 104, 105 are partially formed as shown in FIG. 18B, such that the metal films 104, 105 overlap and join together in a relatively large rhombus area including the place where the probe 102 is located, whereby this overlapping portion constitutes a thermocouple. Accordingly, the probe 106 of the micromechanical sensor shown in FIGS. 18A and 18B is constituted by the probe 102, made of silicon nitride alone, in the micromechanical sensor for the atomic force microscope; and the metal films 104, 105, formed on the lower face of the probe 102, partially overlapping with each other.

In each of the micromechanical sensor shown in FIGS. 16A and 16B and the micromechanical sensor shown in FIGS. 18A and 18B, since their probe is provided with a thermocouple as mentioned above, an image of irregularities of a sample and temperature distribution or thermal conductivity distribution of the sample can be obtained at the same time. These micromechanical sensors, however, have both merits and demerits as explained in the following.

In the micromechanical sensor shown in FIGS. 16A and 16B, as can be seen from the foregoing explanations, the size and position of the thermocouple are determined by the size and position of the opening 11a in the silicon nitride film 11 formed on the substrate 10. As explained above, the opening 11a can be formed by use of lithography technique (employing an exposure apparatus) and dry-etching technique. Consequently, the opening 11a can be formed with a very high accuracy in its size and position, and its area can be made small. Accordingly, the thermocouple can be formed with a very high accuracy in its size and position, and its area can be made small. As a result, the micromechanical sensor shown in FIGS. 16A and 16B yields high accuracy and resolution in measurement of temperature distribution and thermal conductivity distribution in sample surfaces.

Figure 19A:
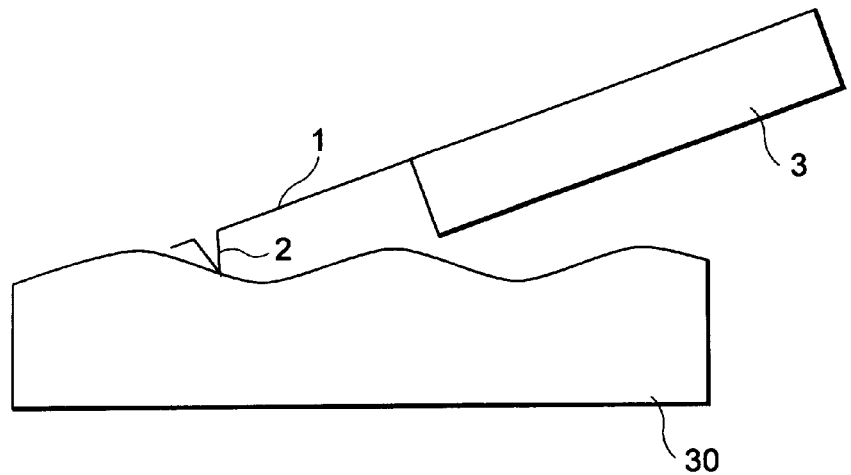
FIG. 19A is a schematic sectional view schematically showing how a surface of a sample 30 is measured by the micromechanical sensor shown in FIGS. 16A and 16B.

However, since the probe 2 and the substrate 3 project from the flexible plate 1 in the same direction, the micromechanical sensor shown in FIGS. 16A and 16B has the following shortcomings. FIG. 19A is a schematic sectional view schematically showing how a surface of a sample 30 is measured by the micromechanical sensor shown in FIGS. 16A and 16B. As shown in FIG. 19A, it is necessary for the probe 2 disposed in the tip side area of the flexible plate 1 to come into contact with or close to the surface of the sample 30 upon measurement. At this time, in the micromechanical sensor shown in FIGS. 16A and 16B, since the probe 2 and the substrate 3 project from the flexible plate 1 in the same direction, a front corner portion of the substrate 3 is likely to abut to the sample 30. In order to avoid this problem, the portion of the flexible plate 1 (i.e., lever portion) not joined to the substrate 3 has to be made relatively long. As is well known, it is desirable in a scanning probe microscope that the resonance frequency of the micromechanical sensor be made higher in order to realize high-speed scanning. Since the lever portion has to be made longer as mentioned above, however, the scanning speed must be made slower, e.g., to about 1/50.

Figure 19B:
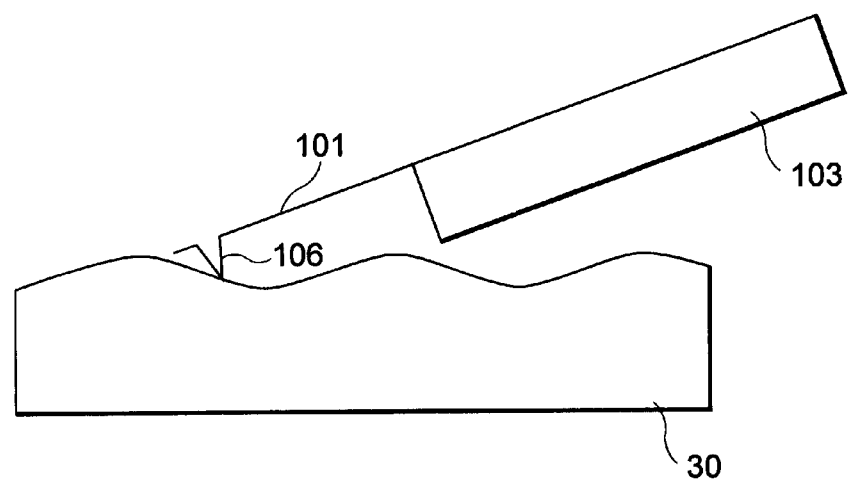
FIG. 19B is a schematic sectional view schematically showing how the surface of the sample 30 is measured by the micromechanical sensor shown in FIGS. 18A and 18B.

In the micromechanical sensor shown in FIGS. 18A and 18B, on the other hand, since the probe 106 and the substrate 103 project from the flexible plate 101 in the directions opposite to each other, the corner portions of the flexible plate 103 are prevented from abutting to the sample 30 as shown in FIG. 19B, whereby the portion of the flexible plate 101 (i.e., lever portion) not joined to the substrate 103 can be made shorter, so as to enhance the resonance frequency of the micromechanical sensor, thus allowing high-speed scanning to be realized. FIG. 19B is a schematic sectional view schematically showing how the surface of the sample 30 is measured by the micromechanical sensor shown in FIGS. 18A and 18B.

In the micromechanical sensor shown in FIGS. 18A and 18B, while the metal films 104, 105 are formed on the probe-side face of the micromechanical sensor for an atomic force microscope, these metal films 104, 105 must be formed by mask vapor deposition or the like. As a consequence, the overlapping portion between the metal films 104, 105 (i.e., thermocouple) cannot be formed with a considerably high accuracy in their size and position, and the thermocouple must have a large area. Consequently, in the micromechanical sensor shown in FIGS. 18A and 18B, the accuracy and resolution in measurement of temperature distribution and thermal conductivity distribution in sample surfaces would decrease.

In the micromechanical sensors shown in FIGS. 1A to 15F, by contrast, accuracy in size and position of the thermocouple can be enhanced so as to improve the accuracy and resolution in measurement of temperature distribution and thermal conductivity distribution in sample surfaces, and the resonance frequency can be made higher since the probe and the substrate project from the flexible plate in the directions opposite to each other, thereby allowing high-speed scanning.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A micromechanical sensor used for a scanning probe microscope, comprising:
   (A) a substrate; and
   (B) first and second cantilever beams each extending from said substrate with one end thereof fixed to said substrate, wherein said cantilever beams respectively have resonance frequency different from each other, and wherein each of said first and second cantilever beams has a probe at a tip portion thereof, the surface of said probe being exposed.

2. A micromechanical sensor according to claim 1, wherein each of said first and second cantilever beams has a probe at a tip portion thereof, said probe comprising a thermocouple.

3. A micromechanical sensor according to claim 2, wherein said thermocouple comprises two kinds of metals joined together, one of said metals containing Ti, while the other containing NiCr.

4. A micromechanical sensor used for a scanning probe microscope, comprising:
   (A) a substrate;
   (B) a cantilever beam extending from said substrate with one end thereof fixed to said substrate, said cantilever beam having an insulting film and a probe, said probe including a thermocouple at a tip portion thereof, said thermocouple including first and second metals joined together, said first metal of said thermocouple being electrically connected to a first conductive film formed on a first surface of said insulting film, said second metal of said thermocouple being electrically connected to a second conductive film formed on a second surface of said insulating film; and
   (C) a bonding pad formed on said first conductive film.

5. A micromechanical sensor according to claim 4,
   wherein said first metal and first conductive film are made from the same metallic material;
   wherein said second metal and second conductive film are made from the same metallic material;
   wherein one of said first and second metal includes a material selected from the group consisting of Me, Al, Si, Ti, V, Cr, Mn, Fe, Co, Ni, Cu, Zn, Ga, Ge, Mo, Pd, Ag, Cd, In, Sn, Sb, Te, W, Ta, Ir, Pt, Au, Pd, and Rh; and
   wherein the materials of said first and second metals are different.

6. A micromechanical sensor according to claim 5,
   wherein said first metal and first conductive film contain Ti; and
   wherein said second metal and second conductive film contain NiCr.

\* \* \* \* \*